(12) United States Patent
Chung et al.

(10) Patent No.: US 12,234,475 B2
(45) Date of Patent: Feb. 25, 2025

(54) COMPOSITIONS AND METHODS FOR THERAPEUTIC DELIVERY

(71) Applicant: GenVivo, Inc., San Marino, CA (US)

(72) Inventors: Brile Chung, San Marino, CA (US); Cecilia Roh, South Pasadena, CA (US); Robert G. Johnson, Jr., Lafayette, CA (US)

(73) Assignee: GenVivo, Inc., San Marino, CA (US)

( * ) Notice: Subject to any disclaimer, the term of this patent is extended or adjusted under 35 U.S.C. 154(b) by 38 days.

(21) Appl. No.: 18/049,266

(22) Filed: Oct. 24, 2022

(65) Prior Publication Data

US 2023/0265457 A1  Aug. 24, 2023

Related U.S. Application Data

(60) Provisional application No. 63/413,165, filed on Oct. 4, 2022, provisional application No. 63/271,674, filed on Oct. 25, 2021.

(51) Int. Cl.
| | |
|---|---|
| *C12N 15/86* | (2006.01) |
| *A61K 31/522* | (2006.01) |
| *A61P 35/00* | (2006.01) |
| *C07H 21/04* | (2006.01) |

(52) U.S. Cl.
CPC ............ *C12N 15/86* (2013.01); *A61K 31/522* (2013.01); *A61P 35/00* (2018.01); *C07H 21/04* (2013.01); *C12N 2740/10043* (2013.01); *C12N 2740/10071* (2013.01)

(58) Field of Classification Search
CPC .. A61K 48/005; A61K 48/0058; C12N 15/86; C12N 2740/10043; C12N 2740/10071; C07H 21/04
See application file for complete search history.

(56) References Cited

U.S. PATENT DOCUMENTS

| | | | |
|---|---|---|---|
| 6,825,033 B2 | 11/2004 | Gordon et al. | |
| 7,632,509 B2 | 12/2009 | Fang et al. | |
| 7,820,157 B2 | 10/2010 | Hall et al. | |
| 10,350,302 B2 | 7/2019 | Levy et al. | |
| 10,610,603 B2 | 4/2020 | Levy et al. | |
| 2001/0046491 A1 | 11/2001 | Valerie | |
| 2003/0004405 A1 | 1/2003 | Townsend et al. | |
| 2003/0008398 A1 | 1/2003 | Mueller et al. | |
| 2004/0229361 A1 | 11/2004 | Mason | |
| 2005/0130132 A1 | 6/2005 | Day et al. | |
| 2006/0216299 A1 | 9/2006 | Hitoshi et al. | |
| 2009/0123428 A1 | 5/2009 | Hall et al. | |
| 2009/0176260 A1 | 7/2009 | Wu et al. | |
| 2009/0285783 A1 | 11/2009 | Freytag et al. | |
| 2010/0135902 A1 | 6/2010 | Roberts et al. | |
| 2010/0233078 A1 | 9/2010 | Szalay et al. | |
| 2010/0322861 A1 | 12/2010 | Gambhir et al. | |
| 2011/0178282 A1 | 7/2011 | Freytag et al. | |
| 2011/0189159 A1 | 8/2011 | Chatterjee et al. | |
| 2013/0011903 A1 | 1/2013 | Black | |
| 2013/0263296 A1 | 10/2013 | Pomper et al. | |
| 2014/0369958 A1 | 12/2014 | Basile | |
| 2018/0369404 A1 | 12/2018 | Larson et al. | |
| 2020/0283778 A1 | 9/2020 | Shah et al. | |
| 2020/0325492 A1 | 10/2020 | O'Shea et al. | |
| 2021/0052647 A1 | 2/2021 | Hinrichs et al. | |

FOREIGN PATENT DOCUMENTS

| | | |
|---|---|---|
| EP | 1914304 A1 | 4/2008 |
| KR | 20110005336 A | 1/2011 |
| WO | WO-2007109335 A2 | 9/2007 |
| WO | WO-2008054826 A2 | 5/2008 |
| WO | WO-2010071587 A1 | 6/2010 |
| WO | WO 2017/040815 A1 * | 3/2017 |
| WO | WO 2018/150345 A1 * | 8/2018 |
| WO | WO-2023076177 A2 | 5/2023 |

OTHER PUBLICATIONS

Kotterman et al., 2014 (Nature Reviews, vol. 15, p. 445-451).*
Shim et al., 2017 (Current Gene Therapy, vol. 17, No. 5, p. 1-18).*
Lenzi et al., 2014 (NCBI Bookshelf, a Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16).*
Bulcha et al., 2021 (Signal Transduction and Targeted Therapy, 6:53, p. 1-24).*
Tsai et al., 2010 (Cancer Gene Therapy, vol. 17, p. 37-48).*
Burkart et al., 2018 (Gene Therapy, 25: 93-103).*
Upadhayaya et al., 2018 (Geneseq Accession No. BFP96381, computer printout, p. 1) (Upadhayaya SEQ ID No. 3).*
Stout et al., 2020 (Geneseq Accession No. BIS03946, computer printout, p. 1).*
Berraondo et al.: Revisiting Interleukin-12 as a Cancer Immunotherapy Agent. Clin Cancer Res. 24(12):2716-2718 doi:10.1158/1078-0432.CCR-18-0381 (2018).
Bridgewood et al.: The novel cytokine MetrnI/IL-41 is elevated in Psoriatic Arthritis synovium and inducible from both entheseal and synovial fibroblasts. Clin Immunol. 208:108253 doi:10.1016/j.clim.2019.108253 [1-5] (2019).

(Continued)

*Primary Examiner* — Shin Lin Chen
(74) *Attorney, Agent, or Firm* — Wilson Sonsini Goodrich & Rosati

(57) ABSTRACT

Described herein are compositions comprising a recombinant retroviral vector for delivering a therapeutic comprising a nucleic acid construct comprising a polynucleotide sequence encoding an interleukin or a subunit thereof. Also described herein are methods of using the composition comprising a recombinant retroviral vector described herein for delivering a therapeutic comprising a nucleic acid construct comprising a polynucleotide sequence encoding an interleukin or a subunit thereof to a subject.

17 Claims, 20 Drawing Sheets

Specification includes a Sequence Listing.

(56) References Cited

OTHER PUBLICATIONS

Del Vecchio et al., Interleukin-12: biological properties and clinical application. Clin Cancer Res 13(16):4677-4685 (2007).
Nakao et al.: Intratumoral expression of IL-7 and IL-12 using an oncolytic virus increases systemic sensitivity to immune checkpoint blockade. Sci Transl Med. 12(526):eaax7992 doi:10.1126/scitranslmed. aax7992 [1-14] (2020).
Nguyen et al.: Localized Interleukin-12 for Cancer Immunotherapy. Front Immunol. 11:575597 doi:10.3389/fimmu.2020.575597 [1-36] (2020).
Wang et al.: Re-designing Interleukin-12 to enhance its safety and potential as an anti-tumor immunotherapeutic agent. Nat Commun. 8(1):1395 doi:10.1038/s41467-017-01385-8 [1-15] (2017).
PCT/US2022/047596 International Search Report and Written Opinion dated Jun. 29, 2023.
Balzarini et al.: Engineering of a single conserved amino acid residue of herpes simplex virus type 1 thymidine kinase allows a predominant shift from pyrimidine to purine nucleoside phosphorylation. Journal of Biological Chemistry 281(28):19273-19279 (2006).
Bottger, et al., "The central half of Pit2 is not required for its function as a retroviral receptor." J Virol. Sep. 2004;78(17):9564-9567.
Degreve, et al., Differential intracellular compartmentalization of herpetic thymidine kinases (TKs) in TK gene-transfected tumor cells: molecular characterization of the nuclear localization signal of herpes simplex virus type 1 TK. Journal of Virology, 72(12):9535-9543, 1998.
Degreve et al., Selective abolishment of pyrimidine nucleoside kinase activity of herpes simplex virus type 1 thymidine kinase by mutation of alanine-167 to tyrosine. Molecular Pharmacology, 58(6):1326-1332, 2000.
Grabarczyk et al., "Expression of PiT-1 and PiT-2 retroviral receptors and transduction efficiency of tumor cells." Acta Biochim. Pol. 2002; 49:333-339.
Likar et al., PET imaging of HSV1-tk mutants with acquired specificity toward pyrimidine- and acycloguanosine-based radiotracers. Eur J Nucl Med Mol Imaging, 36:1273-1282, 2009.
Luker, et al., "Noninvasive imaging of protein-protein interactions in living animals." Proc Natl Acad Sci U S A. May 1, 20024;99(10):6961-6966.
Najjar, et al., "Molecular-genetic PET imaging using an HSV1-tk mutant reporter gene with enhanced specificity to acycloguanosine nucleoside analogs." J Nucl Med. Mar. 2009;50(3):409-416.
Ponomarev, et al., "A novel triple-modality reporter gene for whole-body fluorescent, bioluminescent, and nuclear noninvasive imaging." Eur J Nucl Med Mol Imaging. May 2004;31(5): 740-751.
Ponomarev et al., Cytoplasically retargeted HSV-tk/GFP reporter gene mutants for optimization of noninvasive molecular-genetic imaging NeoplaSIA, 5(3):245-254 (2003).
Serganova et al., Human reporter genes: potential use in clinical studies. Nuclear Medicine and Biology, 34:791-807, 2007.
Skotzko et al., Retroviral vector-mediated gene transfer of antisense cyclin G1 (CYCG1) inhibits proliferation of human osteogenic sarcoma cells. Cancer Research, 55:5493-5498, 1995.
Willmon et al., The role of herpes simplex virus-1 thymidine kinase alanine 168 in substrate specificity. The Open Biochemistry Journal, 2:60-66, 2008.
Yaghoubi, et al., "Noninvasive detection of therapeutic cytolytic T cells with 18F-FHBG Pet in a patient with glioma." Nat Clin Pract Oncol. Jan. 2009;6(1):53-58.

* cited by examiner

Subcutaneous Implantation of CT26
(Luc+) or CT26 mIL-12 (Luc+) Cells

Weekly BLI Imaging
and Survival Curve

Control Group : CT26 (luciferase+) 1.5 x $10^5$ cells (10 mice)

IL-12 Group: CT26 (luciferase+ mIL-12) 1.5 x $10^5$ cells (10 mice)

CT26 mIL-12 Tumor Tissue

Figure Legend
CD8 Cytotoxic T Cell: Green Dye
CD11b Myeloid Cell: Red Dye
Dapi: Blue Dye
Co-localized/overlapping (example) →
Orange-yellow Control CT26 Tumor Tissue P35 retrovector

COMPOSITIONS AND METHODS FOR THERAPEUTIC DELIVERY

CROSS-REFERENCE

This application claims the benefit of U.S. Provisional Application No. 63/271,674 filed on Oct. 25, 2021, and U.S. Provisional Application No. 63/413,165 filed on Oct. 4, 2022, the entirety each of which is hereby incorporated by reference herein.

SEQUENCE LISTING

The instant application contains a Sequence Listing which has been submitted electronically in XML format and is hereby incorporated by reference in its entirety. Said XML copy, created on Apr. 20, 2023, is named 30863-730_201_SL.xml and is 16,404 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BACKGROUND

Interleukin (IL)-12 has been studied as a potential immunotherapy for cancer as it is a T-cell stimulant that can activate anti-cancer T cells. IL-12 promotes development of anti-tumor T-cells by inducing production of certain inflammatory cytokines such as IFN-γ, IL-2, or TNF-α.

SUMMARY

Due to limitations of the IL therapeutics currently available, there remains a need for compositions and methods of treating a subject in need thereof with IL. Accordingly, described herein, in some aspects, is a vector expressing IL-12 that confers advantage over the currently available IL therapeutics. First, IL-12 proteins are not directly injected into a subject, providing no potential systemic dose-limiting toxicities. Moreover, local injection of IL-12 expressing vectors would control the expression level in the tumor area.

The present disclosure provides a recombinant retroviral vector containing polynucleotide sequences separately encoding P40 and P35 subunits of IL-12, and additional polynucleotide sequences in between. The P40 and P35 subunits are individually expressed, and then come together to form a heterodimer linked by disulfide bridges and become functional. In some embodiments, the additional polynucleotide sequences include a cleavage site between P40 subunit and P35 subunit. The contemplated cleavage sites include a furin cleavage site, a self-cleaving peptide (e.g., T2A, P2A, E2A, F2A, or any combination), or both. In some other embodiments, the vector comprises only one polynucleotide sequence encoding an interleukin or a subunit of an interleukin. The present disclosure also provides methods for treating cancer or other disease or condition (e.g., inflammation or infection) in a subject, by administering to the subject any of the retroviral vectors disclosed herein.

Described herein, in some aspects, is a recombinant retroviral vector comprising a nucleic acid construct comprising a first polynucleotide sequence encoding P40 subunit of IL-12, a second polynucleotide sequence encoding P35 subunit of IL-12, and a third polynucleotide sequence between the first and second polynucleotide sequences, wherein the third polynucleotide sequence encodes a cleavage site that facilitates cleavage between P40 subunit and P35 subunit. In some embodiments, the cleavage site comprises a furin cleavage site. In some embodiments, the furin cleavage site comprises the amino acid sequence RRKR. In some embodiments, the nucleic acid construct further comprises a fourth polynucleotide sequence between the first and second polynucleotide sequences, wherein the fourth polynucleotide sequence encodes a self-cleaving peptide. In some embodiments, the self-cleaving peptide comprises a T2A peptide, a P2A peptide, a E2A peptide, a F2A peptide, or a combination thereof. In some embodiments, the T2A peptide comprises an amino acid sequence EGRGSLLTCGDVEENPGP. In some embodiments, the self-cleaving peptide comprises a T2A peptide comprising the amino acid sequence GSGEGRGSLLTCGDVEENPGP. In some embodiments, the P2A peptide comprises the amino acid sequence ATNFSLLKQAGDVEENPGP. In some embodiments, the P2A peptide comprises the amino acid sequence GSGATNFSLLKQAGDVEENPGP. In some embodiments, the E2A peptide comprises the amino acid sequence QCTNYALLKLAGDVESNPGP. In some embodiments, the E2A peptide comprises the amino acid sequence GSGQCTNYALLKLAGDVESNPGP. In some embodiments, the F2A peptide comprises the amino acid sequence VKQTLNFDLLKLAGDVESNPGP. In some embodiments, the F2A peptide comprises the amino acid sequence GSGVKQTLNFDLLKLAGDVESNPGP. In some embodiments, the third polynucleotide sequence is upstream to the fourth polynucleotide sequence. In some embodiments, the nucleic acid construct further comprises a fifth polynucleotide sequence between the third and fourth polynucleotide sequences, wherein the fifth polynucleotide sequence encodes the amino acid sequence GSG. In some embodiments, the first polynucleotide sequence is upstream to the second polynucleotide sequence. In some embodiments, the nucleic acid construct comprises a first start codon immediately upstream to the first polynucleotide sequence, and a second start codon immediately upstream to the second polynucleotide sequence. In some embodiments, the nucleic acid construct further comprises a sixth polynucleotide sequence downstream to the first and second polynucleotide sequences, wherein the sixth polynucleotide sequence encodes a His tag or a FLAG-tag. In some embodiments, the nucleic acid construct further comprises a polynucleotide sequence encoding a thymidine kinase. In some embodiments, the thymidine kinase is in a mutated form with increased cell kill activity relative to a wild-type thymidine kinase. In some embodiments, the nucleic acid construct further comprises a polynucleotide sequence encoding IL-7.

Described herein, in some aspects, is a method for treating cancer in a subject, said method comprises administering to the subject a therapeutically effective amount of a pharmaceutical composition comprising the recombinant retroviral vector described herein. In some embodiments, the method further comprises administering to the subject a therapeutically effective amount of a pharmaceutical composition comprising a recombinant retroviral vector comprising a nucleic acid construct comprising a polynucleotide sequence encoding a thymidine kinase, and co-administering a nucleoside agent. In some embodiments, the polynucleotide sequence encoding the thymidine kinase and the polynucleotide sequence encoding Interleukin-12 are in the same recombinant retroviral vector. In some embodiments, the polynucleotide sequence encoding a thymidine kinase and the polynucleotide sequence encoding Interleukin-12 are in different recombinant retroviral vectors. In some embodiments, the method further comprises monitoring Interleukin-12 level in the subject and inhibiting Interleukin-12 expression in the subject when Interleukin-12 level in the subject reaches a predetermined threshold. In some embodiments, the nucleoside agent is at least one of ganciclovir, valganciclovir, acyclovir, valacyclovir, or penciclovir. In some embodiments, the recombinant retroviral vector encoding the thymidine kinase and the recombinant retroviral vector encoding Interleukin-12 are administered at different time points to the subject.

The novel features of the disclosure are set forth with particularity in the appended claims. A better understanding of the features and advantages of the present disclosure will be obtained by reference to the following detailed description that sets forth illustrative embodiments.

DETAILED DESCRIPTION

Overview

Figure 2:
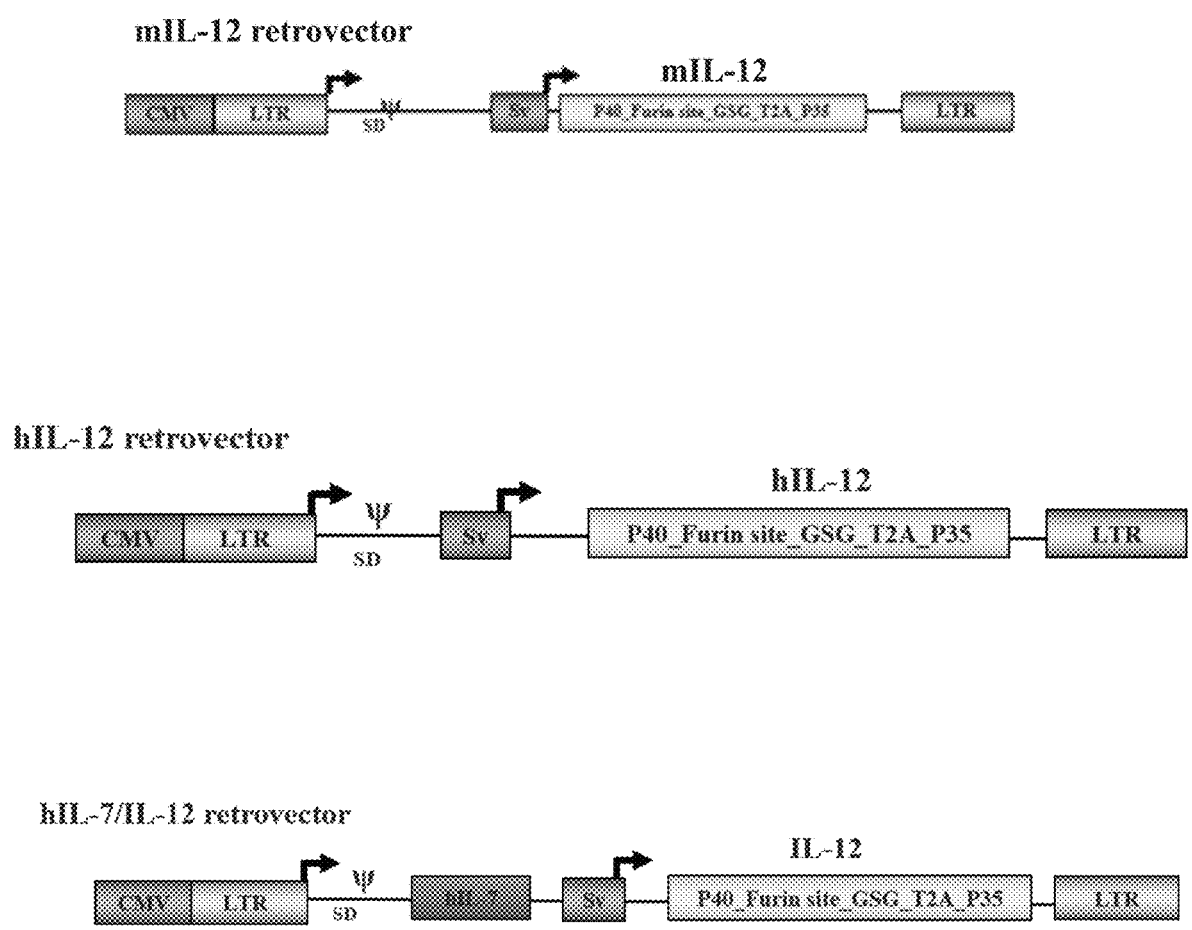
FIG. 2 illustrates an exemplary vectors (vector encoding mouse IL-12, mIL-12, top; vector encoding human IL-12, hIL-12, middle; and vector encoding human IL-7, hIL-7 with IL-12) describe herein.
Figure 3:
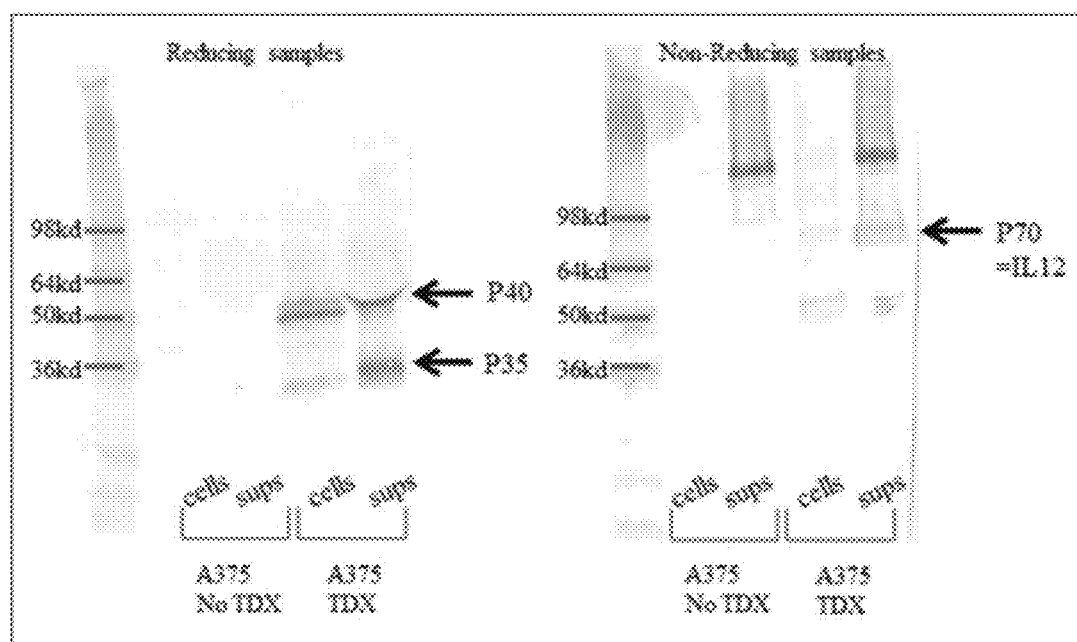
FIG. 3 illustrates mIL-12 expression by Western Blotting.

Described herein, in some aspects, are vectors and methods of using the vectors for expressing a therapeutic in a subject in need thereof. In some aspects, the vector can be formulated into a composition or a pharmaceutical composition. In some aspects, the vector is a recombinant retroviral vector. In some aspects, the vector encodes at least one interleukin (IL) or a subunit of the IL. FIG. 2 illustrates an exemplary recombinant retroviral vector (mIL-12 retrovector) showing nucleic acid encoding IL-12 (mIL-12) described herein. In some aspects, the vector encodes at least two subunits of the IL. In some aspects, the vector encodes a cleavage site, where, upon cleavage event, the at least two subunits of IL encoded by the vector are cleaved. In some aspects, the cleavage site comprises a self-cleavage site (e.g., a ribozyme site or a self-cleaving peptide). In some aspects, the cleavage site comprises a peptide cleavage site, where the at least two subunits of IL can be cleaved by an endogenous or an exogenous protease or by self-cleavage. In some aspects, the cleaved IL subunits can be complexed to each other to form functional IL. In some aspects, the cleaved IL subunits can be complexed with other endogenous IL subunits to form functional IL. In some embodiments, the IL belongs to IL-12 family, including IL-12, IL-23, IL-27, IL-35, or IL-39. In some embodiments, the IL is IL-12. In some embodiments, the IL-12 comprises a heterodimer comprising a P40 subunit and a P35 subunit. In some embodiments, the IL is IL-7. In some aspects, the vector encodes IL-12 either as two IL-12 subunits (which then dimerize to form IL-12 as or as a single recombinant IL-12 (FIG. 3). In some aspects, the vector comprises a retroviral vector. In some aspects, the vector encodes an enzyme that can convert a prodrug nucleoside agent into a cytotoxic drug for treating the disease or condition.

Also described herein, in some aspects, is a method for treating a subject in need thereof. In some aspects, the method comprises administering the subject at least one vector encoding the at least one IL subunit. In some aspects, the method comprises administering the subject at least one vector encoding the at least one IL subunit and the enzyme that converts a prodrug nucleoside agent. In some aspects, the method comprises formulating the vector described herein into a composition or a pharmaceutical composition to be administered into the subject in need thereof. In some aspects, the method described herein comprises contacting a cell ex vivo with the at least one vector, for expressing the at least one IL subunit or the enzyme described herein (e.g., a thymidine kinase) that can convert a prodrug nucleoside agent into a cytotoxic drug in the cell. In some aspects, the method comprises administering the cell contacted with the at least one vector to the subject in need thereof, where the cell expresses and delivers the at least one IL subunit or the enzyme described herein to the subject, thereby treating the subject with the disease or condition.

In some aspects, the disease or condition is cancer (e.g., neoplasia, tumor, or lesion). In some aspects, described herein is a method for treating cancer in the subject by contacting the cancer cell or tumor with the interleukin (e.g., IL-12 or IL-7) and/or the enzyme capable of converting a prodrug into a cytotoxic drug, where, upon contacting with the interleukin and/or the enzyme, the tumor is converted from cold tumor to hot tumor. In some aspects, cold tumor is tumor or cancer cell that lacks significant immunological activity, which can indicate a relatively high degree of tolerance by the immune system for the presence of the tumor. Such tolerance can negatively impact any cancer treatment modality that would depend on a robust immune response directed towards such cold tumor or cancer cells. In some aspects, hot tumor is tumor or cancer cell that shows an increased level of immunologic activity that can support treatment modalities dependent on a relatively low tolerance by the immune system by tumor cells. The method described herein leverages the potential for a vector described herein to deliver a localized expression of interleukin (e.g., IL-12 or IL-7) with the intent of converting cold tumors to hot tumor. Such conversion can render tumor or cancer cell susceptible to an immune response from the subject being treated with the vector described herein.

In some embodiments, the disease or condition is inflammation or infection (e.g., infection by bacterium, protozoan, mycobacterium, fungus, or virus). In some embodiments, the disease or condition is inflammation caused by infection.

Vector

Described herein, in some aspects, is a recombinant retroviral vector comprising a nucleic acid construct comprising at least one polynucleotide sequence encoding an interleukin, a subunit of an interleukin, or a combination thereof. In some embodiments, the vector encodes at least one interleukin subunit. In some embodiments, the vector encodes at least two interleukin subunits, where the at least two interleukin subunits are the same or different. In some embodiments, the vector encodes one interleukin subunit. In some embodiments, the vector encodes two interleukin subunits. In some embodiments, the vector encodes two different interleukin subunits. In some embodiments, the vector encodes two or more different interleukin subunits. In some embodiments, the vector comprises at least one start codon for expressing the interleukin, the subunit of the interleukin, or a combination thereof. In some embodiments, the vector comprises at least two start codons for expressing two interleukins, two subunits of the interleukin, or a combination thereof. In some embodiments, the vector comprises two codons each for expressing an interleukin subunit. In some aspects, the vector encodes at least one additional enzyme that is not an interleukin. In some embodiments, the vector is a retroviral vector. In some aspects, the expression of the interleukin, the subunit of an interleukin, the at least one additional enzyme, or a combination thereof encoded by the vector can occur in vivo. For example, the interleukin, the subunit of an interleukin, the at least one additional enzyme, or the combination thereof can be expressed in vivo in a subject in need thereof by administering the vector either directly or as a composition (e.g., a pharmaceutical composition) described herein to the subject. In some embodiments, the vector can be first introduced into the cell ex vivo for expressing the interleukin, the subunit of an interleukin, the at least one additional enzyme, or a combination thereof. In some aspects, the cell comprising the vector can then be administered to the subject in need thereof, where the administered cell can express the interleukin, the subunit of an interleukin, the at least one additional enzyme, or a combination thereof in vivo in the subject in need thereof.

In some embodiments, the vector comprises at least one polynucleotide encoding an interleukin, a subunit of an interleukin, or a combination thereof. Non-limiting example of the interleukin can include IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, IL-39, IL-40, or IL-41. In some embodiments, the interleukin comprises IL-7. In some embodiments, the interleukin comprises IL-12. In some embodiments, the vector comprises a first polynucleotide sequence encoding P40 subunit of Interleukin-12 (IL-12) and a second polynucleotide sequence encoding P35 subunit of IL-12. In some aspects, the vector comprises a third polynucleotide sequence between the first and the second polynucleotide sequences, where the third polynucleotide sequence encodes a cleavage site that facilitates cleavage between P40 subunit and P35 subunit. In some aspects, the third polynucleotide sequence encodes a peptide cleavage site. In some embodiments, the cleavage site can be targeted and cleaved by an endogenous protease. In some embodiments, the endogenous protease comprises a furin. In some embodiments, the cleavage site is a furin cleavage site comprising an amino acid sequence of RXYR, where R is arginine and Y can be arginine or lysine. In some embodiments, the cleavage site comprises an amino acid sequence of RRKR. In some embodiments, the cleavage site comprises an amino acid sequence of RKRR.

In some aspects, the peptide cleavage site is a self-cleaving peptide such as T2A, P2A, E2A, or F2A. In some embodiments, the peptide cleavage site comprises a T2A peptide comprising an amino acid sequence: EGRGSLLTCGDVEENPGP. In some embodiments, the peptide cleavage site comprises a T2A peptide comprising an amino acid sequence: GSGEGRGSLLTCGDVEENPGP. In some embodiments, the peptide cleavage site comprises a P2A peptide comprising an amino acid sequence: ATNFSLLKQAGDVEENPGP. In some embodiments, the peptide cleavage site comprises a P2A peptide comprising an amino acid sequence: GSGATNFSLLKQAGDVEEN- PGP. In some embodiments, the peptide cleavage site comprises a E2A peptide comprising an amino acid sequence: QCTNYALLKLAGDVESNPGP. In some embodiments, the peptide cleavage site comprises a E2A peptide comprising an amino acid sequence: GSGQCTNYALLKLAGDVESNPGP. In some embodiments, the peptide cleavage site comprises a F2A peptide comprising an amino acid sequence: VKQTLNFDLLKLAGDVESNPGP. In some embodiments, the peptide cleavage site comprises a F2A peptide comprising an amino acid sequence: GSGVKQTLNFDLLKLAGDVESNPGP.

In some embodiments, the vector comprises only one polynucleotide sequence encoding an interleukin or a subunit of an interleukin. For example, the vector can comprise encode only a subunit of an interleukin such as IL-12. As showing in FIGS. 18-20, the retroviral vector encoding P35 subunit of IL-12 was sufficient to induce or increase expression of IL-12. In some embodiments, the vector encoding an interleukin or a subunit of an interleukin can decrease toxicity associated with interleukin therapeutics. In some embodiments, the vector encoding an interleukin or a subunit of an interleukin can decrease toxicity associated with interleukin therapeutics due to expression of the subunit of the interleukin. In some embodiments, the vector encoding an interleukin or a subunit of an interleukin can decrease toxicity associated with interleukin therapeutics without decreasing therapeutic efficacy of the interleukin. In some embodiments, the vector encoding an interleukin or a subunit of an interleukin can decrease toxicity associated with interleukin therapeutics by modulating the expression or abundance of interleukin. For example, the vector encoding an interleukin or a subunit of an interleukin can decrease toxicity associated with interleukin therapeutics by modulating the expression or abundance of in vivo interleukin in a subject in need of treatment of interleukin therapeutics.

In some embodiments, the vector comprises at least one promoter for expressing the at least one polynucleotide. For example, the vector comprises a CMV promoter for expressing the at least one polynucleotide encoding the interleukin (e.g., the P40 subunit and the P35 subunit) described herein. Other example of the promoter can include the retroviral LTR; the SV40 promoter; the Rous Sarcoma Virus (RSV) promoter; the histone promoter; the polIII promoter, the β-actin promoter; inducible promoters, such as the MMTV promoter, the metallothionein promoter; heat shock promoters; adenovirus promoters; the albumin promoter; the ApoAI promoter; B19 parvovirus promoters; human globin promoters; viral thymidine kinase promoters, such as the Herpes Simplex Virus thymidine kinase promoter; retroviral LTRs; human growth hormone promoters, and the MxIFN inducible promoter. In some embodiments, the promoter is a tissue-specific promoter. In some embodiments, a tissue specific promoters is chosen from the group including the tyrosinase related promoters (TRP-1 and TRP-2), DF3 enhancer (for breast cells), SLPI promoter (secretory leucoprotease inhibitor-expressed in many types of carcinomas), TRS (tissue specific regulatory sequences), α-fetoprotein promoters (specific for normal hepatocytes and transformed hepatocytes, respectively), the carcino-embryonic antigen promoter (for use in transformed cells of the gastrointestinal tract, lung, breast and other tissues), the tyrosine hydroxylase promoter (for melanocytes), choline acetyl transferase or neuron specific enolase promoters for use in neuroblastomas, the regulatory sequence for glial fibroblastomas, the tyrosine hydroxylase promoter, c-erb B-2 promoter, PGK promoter, PEPCK promoter, whey acidic promoter (breast tissue), and casein promoter (breast tissue) and the adipocyte P2 promoter. In some embodiments, the promoter is a viral-specific promoter (e.g., retroviral promoters, as well as others such as HIV promoters), hepatitis, herpes (e.g., EBV). In some embodiments, the promoter is the native HSV-TK promoter. In some embodiments, the promoter is a bacterial, fungal or parasitic (e.g., malarial)-specific promoter is utilized in order to target a specific cell or tissue which is infected with a virus, bacteria, fungus, or parasite.

In some embodiments, the vector comprises two or more promoters for expressing the interleukin or interleukin subunits separately in a cell. In some aspects, the vector comprises a nucleic acid sequence for encoding a tag such as His tag or a Flag tag for purification, imaging, or expression control purpose.

In some aspects, the vector is a viral vector such as a retroviral vector. Viral vectors, and especially retroviral vectors, have become the most widely used method for inserting genes into mammalian, e.g., human cells. Other viral vectors, in some embodiments, are derived from lentivirus, poxviruses, herpes simplex virus I, adenoviruses, adeno-associated viruses, or Sindbis viruses. Non-limiting examples of viral vectors can include retroviral vectors, adenoviral vectors, adeno-associated viral vectors (AAVs), pox vectors, parvoviral vectors, baculovirus vectors, measles viral vectors, or herpes simplex virus vectors (HSVs). In some instances, the retroviral vectors include gamma-retroviral vectors such as vectors derived from the Moloney Murine Leukemia Virus (MoMLV, MMLV, MuLV, or MLV) or the Murine Stem cell Virus (MSCV) genome. In some instances, the retroviral vectors also include lentiviral vectors such as those derived from the human immunodeficiency virus (HIV) genome. In some instances, AAV vectors include AAV1, AAV2, AAV4, AAV5, AAV6, AAV7, AAV8, or AAV9 serotype. In some instances, viral vector is a chimeric viral vector, comprising viral portions from two or more viruses. In additional instances, the viral vector is a recombinant viral vector.

In some embodiments, the vector encodes a non-interleukin enzyme. In some aspects, the vector encodes an enzyme that can convert a nucleoside agent into a cytotoxic drug for killing a cell associated with the disease or condition described herein. In some embodiments, the enzyme comprises a kinase with nucleic acid nucleotide as a substrate. In some embodiments, the kinase is a thymidine kinase, where the thymidine kinase is salvage pathway enzyme which phosphorylates natural nucleoside substrates as well as nucleoside analogues. Generally, viral thymidine kinase can be exploited therapeutically by administration of a nucleoside analogue such as ganciclovir or acyclovir to a cell expressing viral thymidine kinase, wherein the viral thymidine kinase phosphorylates the nucleoside analogue, creating a toxic product capable of killing the cell. Viral thymidine kinase of the present disclosure can be prepared from a wide variety of viral thymidine kinases. In some embodiments, the viral thymidine kinase mutant is derived from Herpesviridae thymidine kinase including, for example, both primate herpes viruses, and non-primate herpes viruses such as avian herpes viruses. Representative examples of suitable herpes viruses include, for example, Herpes Simplex Virus (HSV) Type 1, Herpes Simplex Virus Type 2, Varicella zoster Virus, marmoset herpes virus, feline herpes virus type 1, pseudorabies virus, equine herpes virus type 1, bovine herpes virus type 1, turkey herpes virus, Marek's disease virus, herpesvirus saimiri, or Epstein-Barr virus.

In some aspects, the thymidine kinase described herein can be a mutant thymidine kinase, where the mutant thymidine kinase comprises at least one amino acid mutation. In some aspects, the mutant thymidine kinase is a mutant Herpes Simplex Virus type 1 thymidine kinase (HSV1-TK) comprising at least one amino acid mutation compared to wild type amino acid sequence of HSV1-TK: MASYPGHQHASAFDQAARSRGHSNRRTALR-PRRQQEATEVRPEQKMPTLLRVYIDGPHGM GKTTTTQLLVALGSRDDIVYVPEPMTYWRVLGAS-ETIANIYTTQHRLDQGEISAGDAAVVM TSAQITMGMPYAVTDAVLAPHIGGEAGSSHAPPPAL-TLIFDRHPIAALLCYPAARYLMGSMT PQAVLAFVA-LIPPTLPGTNIVLGALPEDRHIDRLAKRQRPGERLD-LAMLAAIRRVYGLLANT VRYLQCGGSWREDWGQLSGTAVPPQGAE-PQSNAGPRPHIGDTLFTLFRAPELLAPNGDLYN VFAWALDVLAKRLR (SEQ ID NO: 1). In some aspects, the mutant HSV1-TK comprises an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the HSV1-TK amino acid sequence (e.g., SEQ ID NO: 1). In some embodiments, the mutant HSV-1-TK comprises a nuclear export sequence (NES). In some aspects, the NES comprises an amino acid sequence of LQKKLEELELDG (SEQ ID NO: 2).

In some embodiments, the mutant HSV1-TK comprises at least one amino acid mutation at amino acid residue 25, 26, 32, 33, 167, 168, or a combination thereof compared to the wild type amino acid sequence of HSV1-TK (SEQ ID NO: 1). In some embodiments, the mutation comprises substituting a wild type amino acid with a polar, non-polar, basic or acidic amino acid. In some embodiments, the mutant HSV1-TK is mutated at amino acid residues 167, 168, or both. In one example, the sequence is mutated at amino acid residue 167. In another example, the sequence is mutated at amino acid residue 168. In another example, the sequence is mutated at amino acid residues 167 and 168. Amino acid residue 167 may be mutated to histidine, lysine, cysteine, serine, and phenylalanine. Amino acid residue 168 may be mutated to histidine, lysine, cysteine, serine, or phenylalanine. In some embodiments, the mutant HSV1-TK is mutated at amino acid residues 25 and/or 26. In amino acid residues 25 and/or 26 may be mutated to an amino acid chosen from the group consisting of: glycine, serine, and glutamate. In some embodiments, the mutant HSV1-TK is mutated at amino acid residues 32 and/or 33. Amino acid residues 32 and/or 33 may be mutated to an amino acid chosen from the group consisting of: glycine, serine, cysteine, glutamic acid, and aspartic acid. In some embodiments, the mutant HSV1-TK is mutated at amino acid residues 25, 26, 32, and/or 33. Amino acid residues 25, 26, 32, and/or 33, may be mutated to an amino acid chosen from the group consisting of: glycine, serine, cysteine, glutamic acid, and aspartic acid.

In some embodiments, the mutant HSV1-TK is mutated at amino acid residue: 25 and/or 26; and 167, where the mutation at amino acid residue 25 and/or 26 comprises glycine, serine, cysteine, glutamic acid, or aspartic acid; and the mutation at amino acid residue 167 comprises histidine, lysine, cysteine, serine, or phenylalanine. In some embodiments, the mutant HSV1-TK is mutated at amino acid residue: 25 and/or 26; and 168, where the mutation at amino acid residue 25 and/or 26 comprises glycine, serine, cysteine, glutamic acid, or aspartic acid; and the mutation at amino acid residue 168 comprises histidine, lysine, cysteine, serine, or phenylalanine. In some embodiments, the mutant HSV1-TK is mutated at amino acid residue: 25 and/or 26; and 167 and/or 168, where the mutation at amino acid residue 25 and/or 26 comprises glycine, serine, cysteine, glutamic acid, or aspartic acid; and the mutation at amino acid residue 167 and/or 168 comprises histidine, lysine, cysteine, serine, or phenylalanine.

In some embodiments, the mutant HSV1-TK is mutated at amino acid residue: 32 and/or 33; and 167, where the mutation at amino acid residue 32 and/or 33 comprises glycine, serine, cysteine, glutamic acid, or aspartic acid; and the mutation at amino acid residue 167 comprises histidine, lysine, cysteine, serine, or phenylalanine. In some embodiments, the mutant HSV1-TK is mutated at amino acid residue: 32 and/or 33; and 168, where the mutation at amino acid residue 32 and/or 33 comprises glycine, serine, cysteine, glutamic acid, or aspartic acid; and the mutation at amino acid residue 168 comprises histidine, lysine, cysteine, serine, or phenylalanine. In some embodiments, the mutant HSV1-TK is mutated at amino acid residue: 32 and/or 33; and 167 and/or 168, where the mutation at amino acid residue 32 and/or 33 comprises glycine, serine, cysteine, glutamic acid, or aspartic acid; and the mutation at amino acid residue 167 and/or 168 comprises histidine, lysine, cysteine, serine, or phenylalanine.

In some embodiments, the mutant HSV1-TK is mutated at amino acid residue: 25, 26, 32, and 33; and 167, where the mutation at amino acid residue 25, 26, 32, and 33 comprises glycine, serine, cysteine, glutamic acid, or aspartic acid; and the mutation at amino acid residue 167 comprises histidine, lysine, cysteine, serine, or phenylalanine. In some embodiments, the mutant HSV1-TK is mutated at amino acid residue: 25, 26, 32, and 33; and 168, where the mutation at amino acid residue 25, 26, 32, and 33 comprises glycine, serine, cysteine, glutamic acid, or aspartic acid; and the mutation at amino acid residue 168 comprises histidine, lysine, cysteine, serine, or phenylalanine. In some embodiments, the mutant HSV1-TK is mutated at amino acid residue: 25, 26, 32, and 33; and 167 and/or 168, where the mutation at amino acid residue 25, 26, 32, and 33 comprises glycine, serine, cysteine, glutamic acid, or aspartic acid; and the mutation at amino acid residue 167 and/or 168 comprises histidine, lysine, cysteine, serine, or phenylalanine.

In some embodiments, the mutant HSV1-TK is mutated at amino acid residue: 25 and 26 or 32 and 33; and 167, where the mutation at amino acid residue 25 and 26 or 32 and 33 comprises glycine, serine, cysteine, glutamic acid, or aspartic acid; and the mutation at amino acid residue 167 comprises histidine, lysine, cysteine, serine, or phenylalanine. In some embodiments, the mutant HSV1-TK is mutated at amino acid residue: 25 and 26 or 32 and 33; and 168, where the mutation at amino acid residue 25 and 26 or 32 and 33 comprises glycine, serine, cysteine, glutamic acid, or aspartic acid; and the mutation at amino acid residue 168 comprises histidine, lysine, cysteine, serine, or phenylalanine. In some embodiments, the mutant HSV1-TK is mutated at amino acid residue: 25 and 26 or 32 and 33; and 167 and/or 168, where the mutation at amino acid residue 25 and 26 or 32 and 33 comprises glycine, serine, cysteine, glutamic acid, or aspartic acid; and the mutation at amino acid residue 167 and/or 168 comprises histidine, lysine, cysteine, serine, or phenylalanine.

In some embodiments, the mutant HSV1-TK is mutated at amino acid residue: any one or more of 25, 26, 32 and/or 33; and 167, where the mutation at amino acid residue any one or more of 25, 26, 32 and/or 33 comprises glycine, serine, cysteine, glutamic acid, or aspartic acid; and the mutation at amino acid residue 167 comprises histidine, lysine, cysteine, serine, or phenylalanine. In some embodiments, the mutant HSV1-TK is mutated at amino acid residue: any one or more of 25, 26, 32 and/or 33; and 168, where the mutation at amino acid residue any one or more of 25, 26, 32 and/or 33 comprises glycine, serine, cysteine, glutamic acid, or aspartic acid; and the mutation at amino acid residue 168 comprises histidine, lysine, cysteine, serine, or phenylalanine. In some embodiments, the mutant HSV1-TK is mutated at amino acid residue: any one or more of 25, 26, 32 and/or 33; and 167 and/or 168, where the mutation at amino acid residue any one or more of 25, 26, 32 and/or 33 comprises glycine, serine, cysteine, glutamic acid, or aspartic acid; and the mutation at amino acid residue 167 and/or 168 comprises histidine, lysine, cysteine, serine, or phenylalanine.

In some embodiments, the vector, in addition to encoding mutant HSV1-TK, can encode PiT-2, PiT-1, mCat-1 (murine cationic receptor-1; target of ecotropic Moloney MLV), or other receptors used by gamma retroviruses.

In some embodiments, the mutant HSV1-TK, compared to wild type HSV1-TK, comprises increased enzymatic activity of converting a nucleoside agent into a cytotoxic drug. In some embodiments, the mutant HSV1-TK increases enzymatic activity of converting a nucleoside agent into a cytotoxic drug by at least 0.1 fold, 0.2 fold, 0.3 fold, 0.4 fold, 0.5 fold, 1.0 fold, 2.0 fold, 5.0 fold, 10.0 fold, or more compared to the enzymatic activity of a wild type HSV1-TK converting the same nucleoside agent (e.g., a prodrug) into the cytotoxic drug.

In some embodiments, the mutant HSV1-TK increases bystander effect for killing the cell associated with the disease or condition. As used herein, the "bystander effect" refers to the phenomenon by which a HSV1-TK positive cell (e.g., cell contacted with vector described herein) exerts a kill effect on neighboring HSV1-TK negative cells following induction of expression of HSV1-TK expression in the HSV1-TK positive cells. In some embodiments, the mutant HSV1-TK increases the bystander effect by at least 0.1 fold, 0.2 fold, 0.3 fold, 0.4 fold, 0.5 fold, 1.0 fold, 2.0 fold, 5.0 fold, 10.0 fold, or more compared to the bystander effect induced by a wild type HSV1-TK positive cell.

Method

Disclosed herein, in some embodiments, are methods of using the vector described herein. In some embodiments, the method comprises treating a disease or condition in a subject in need thereof by administering a vector or pharmaceutical composition comprising the vector described herein to the subject. In some embodiments, the method comprises contacting a cell with the vector and subsequently administering the cell to the subject. In some embodiments, the cell contacted with the vector is an autologous cell. For example, the cell can be first isolated from the subject and optionally cultured or expanded prior to being contacted with the vector. In some embodiments, expression of the interleukin (e.g., P40 or P35 of IL-12 or IL-7) or HSV1-TK encoded by the vector can be verified in the cell prior to administering the cell to the subject. FIGS. 11-17 illustrates an in vivo example where the cell contacted with the vector described herein can lead to killing of cancer cells after being translated into a mouse with tumors.

In some embodiments, the method comprises administering two or more vectors to the subject, where a first of the two or more vectors encode an interleukin (e.g., P40 or P35 of IL-12 or IL-7) described herein and a second of the two or more vectors encode a thymidine kinase (e.g., the mutated HSV1-TK) described herein. In some embodiments, the method comprises first contacting a cell with the two or more vectors and subsequently administering the cell of the subject. In embodiments, the interleukin (e.g., P40 or P35 of IL-12 or IL-7) and the thymidine kinase (e.g., the mutated HSV1-TK) are encoded by the same vector. In some embodiments, administration is by any suitable mode of administration, including systemic administration (e.g., intravenous, inhalation, etc.). In some embodiments, the subject is human. In some embodiments, the disease or condition is cancer or lesion. In some embodiments, the two or more vectors can be co-administered. In some embodiments, the two or more vectors can be co-administered at the same time. In some embodiments, the two or more vectors can be co-administered at different time points. For example, a first vector encoding the IL-12 or IL-7 can be administered to the subject followed by administering a second vector encoding the mutant thymidine kinase at a different time point.

In some embodiments, the vector, the cell comprising the vector, or the pharmaceutical composition delivers an interleukin to a cell or microenvironment associated with the disease or condition. In some embodiments, the vector, the cell comprising the vector, or the pharmaceutical composition delivering the interleukin decreases toxicity (e.g. as determined by decreased cell death of cells not associated with the disease or condition or decreased expression of hot tumor genes) in the subject compared to direct administration of interleukin to the subject. In some embodiments, the toxicity of delivering the interleukin by the vector, the cell comprising the vector, or the pharmaceutical composition described herein is decreased by at least 0.1 fold, 0.2 fold, 0.5 fold, 1.0 fold, 2.0 fold, 5.0 fold, 10.0 fold, 50.0 fold, or more compared to toxicity induced by directly administering the interleukin to the subject.

In some embodiments, the vector, the cell comprising the vector, or the pharmaceutical composition delivers an IL-12 or IL-7 to a cell or microenvironment associated with the disease or condition. In some embodiments, the vector, the cell comprising the vector, or the pharmaceutical composition delivering the IL-12 (either as P40 subunit and P35 subunit or as a recombinant IL-12) or IL-7 decreases toxicity (e.g. as determined by decreased cell death of cells not associated with the disease or condition or decreased expression of hot tumor genes) in the subject compared to direct administration of IL-12 or IL-7 to the subject. In some embodiments, the toxicity of delivering the IL-12 or IL-7 by the vector, the cell comprising the vector, or the pharmaceutical composition described herein is decreased by at least 0.1 fold, 0.2 fold, 0.5 fold, 1.0 fold, 2.0 fold, 5.0 fold, 10.0 fold, 50.0 fold, or more compared to toxicity induced by directly administering the IL-12 or IL-7 to the subject.

In some embodiments, the IL-12 or IL-7 encoded by the vector is expressed and secreted by the cell. In some embodiments, the IL-12 or IL-7 expressed or secreted by the cell can stimulate innate immune signaling or response in the subject. In some embodiments, the method comprises stimulating the production of endogenous cytokines (e.g., IFN-γ) with the expressed or secreted interleukin (e.g., P40 or P35 of IL-12 or IL-7) for treating the disease or condition. As shown in FIGS. 5-10, the IL-12 encoded by the recombinant retroviral vector can stimulate cytokine or hot tumor gene expression (e.g., IFN-γ, T-bet, IL-2, IL-15, and TNFα) in splenocytes. Hot tumor gene expression can refer to expression of gene products such as the cytokines described herein that triggers endogenous immune response. As such, the expression of the hot tumor gene can lead to killing of the cell (e.g., a cancer or a tumor cell) associated with the disease or condition by the endogenous immune response.

In some embodiments, the vector comprises only one polynucleotide sequence encoding an interleukin or a subunit of an interleukin. For example, the vector can comprise encode only a subunit of an interleukin such as IL-12. As showing in FIGS. 18-20, the retroviral vector encoding P35 subunit of IL-12 was sufficient to induce or increase expression of IL-12 when P40 was present. In some embodiments, the vector encoding an interleukin or a subunit of an interleukin can decrease toxicity associated with interleukin therapeutics. In some embodiments, the vector encoding an interleukin or a subunit of an interleukin can decrease toxicity associated with interleukin therapeutics due to expression of the subunit of the interleukin. In some embodiments, the vector encoding an interleukin or a subunit of an interleukin can decrease toxicity associated with interleukin therapeutics without decreasing therapeutic efficacy of the interleukin. In some embodiments, the vector encoding an interleukin or a subunit of an interleukin can decrease toxicity associated with interleukin therapeutics by modulating the expression or abundance of interleukin. For example, the vector encoding an interleukin or a subunit of an interleukin can decrease toxicity associated with interleukin therapeutics by modulating the expression or abundance of in vivo interleukin in a subject in need of treatment of interleukin therapeutics.

In some embodiments, the vector, the cell comprising the vector, or the pharmaceutical composition delivering the interleukin increases efficacy for treating the disease or condition (e.g. as determined by increased cell death of tumor cells or increased expression of hot tumor genes) in the subject compared to direct administration of interleukin to the subject. In some embodiments, the efficacy for treating the disease or condition by delivering the interleukin by the vector, the cell comprising the vector, or the pharmaceutical composition described herein is decreased by at least 0.1 fold, 0.2 fold, 0.5 fold, 1.0 fold, 2.0 fold, 5.0 fold, 10.0 fold, 50.0 fold, or more compared to efficacy for treating the disease or condition by directly administering the interleukin to the subject.

In some embodiments, the vector, the cell comprising the vector, or the pharmaceutical composition delivering the IL-12 (either as P40 subunit and P35 subunit or as a recombinant IL-12) or IL-7 increases efficacy for treating the disease or condition (e.g. as determined by increased cell death of tumor cells or increased expression of hot tumor genes) in the subject compared to direct administration of IL-12 or IL-7 to the subject. In some embodiments, the efficacy for treating the disease or condition by delivering the IL-12 or IL-7 by the vector, the cell comprising the vector, or the pharmaceutical composition described herein is decreased by at least 0.1 fold, 0.2 fold, 0.5 fold, 1.0 fold, 2.0 fold, 5.0 fold, 10.0 fold, 50.0 fold, or more compared to efficacy for treating the disease or condition by directly administering the IL-12 or IL-7 to the subject.

In some embodiments, the vector, the cell comprising the vector, or the pharmaceutical composition is administered at least once during a period of time (e.g., every 2 days, twice a week, once a week, every week, three times per month, two times per month, one time per month, every 2 months, every 3 months, every 4 months, every 5 months, every 6 months, every 7 months, every 8 months, every 9 months, every 10 months, every 11 months, once a year). In some embodiments, the composition is administered two or more times (e.g., 2, 3, 4, 5, 6, 7, 8, 9, 10, 11, 12, 13, 14, 15, 16, 17, 18, 19, 20, 30, 40, 50, 60, 70, 80, 90, 100 times) during a period of time.

In some embodiments, the vector, the cell comprising the vector, or the pharmaceutical composition is administered in a therapeutically-effective amount by various forms and routes including, for example, oral, or topical administration. In some embodiments, the vector, the cell comprising the vector, or the pharmaceutical composition may be administered by intratumoral, parenteral, intravenous, subcutaneous, intramuscular, intradermal, intraperitoneal, intracerebral, subarachnoid, intraocular, intrasternal, ophthalmic, endothelial, local, intranasal, intrapulmonary, rectal, intraarterial, intrathecal, inhalation, intralesional, intradermal, epidural, intracapsular, subcapsular, intracardiac, transtracheal, subcuticular, subarachnoid, or intraspinal administration, e.g., injection or infusion. In some embodiments, a composition may be administered by absorption through epithelial or mucocutaneous linings (e.g., oral mucosa, rectal and intestinal mucosa administration). In some embodiments, the vector, the cell comprising the vector, or the pharmaceutical composition is delivered via multiple administration routes.

In some embodiments, the vector, the cell comprising the vector, or the pharmaceutical composition is administered by intravenous infusion. In some embodiments, the vector, the cell comprising the vector, or the pharmaceutical composition comprising the vector is administered by slow continuous infusion over a long period, such as more than 24 hours. In some aspects, the vector, the cell comprising the vector, or the pharmaceutical composition can be administered in a local manner, for example, via injection of the agent directly into an organ, optionally in a depot or sustained release formulation or implant.

In some embodiments, the method comprises monitoring expression of interleukin such as IL-12 or IL-7 in the subject after the subject has been treated. In some aspects, the method comprises monitoring the expression level of IL-12 or IL-7, where, if the IL-12 or IL-7 expression reaches a predetermined threshold in the subject, an interleukin inhibitor can be administered to the subject.

In some embodiments, the vector, the cell comprising the vector, or the pharmaceutical composition provided herein can be administered in conjunction with at least one additional therapeutic, for example, an antiviral therapy, a chemotherapy, an antibiotic, a cell therapy, a cytokine therapy, or an anti-inflammatory agent. In some embodiments, the at least one additional therapeutic comprises a nucleoside agent (e.g., a prodrug). Non-limiting example of the prodrug can include FHBG (9-[4-fluoro-3-(hydroxymethyl)butyl] guanine), FHPG (9-([3-fluoro-1-hydroxy-2-propoxy] methyl)guanine), FGCV (fluoroganciclovir), FPCV (fluoropenciclovir), FIAU (1-(2'-deoxy-2'-fluoro-1-β-D-arabinofuranosyl)-5-iodouracil), FEAU (fluoro-5-ethyl-1-beta-D-arabinofuranosyluracil), FMAU (fluoro-5-methyl-1-beta-D-arabinofuranosyluracil), FHOMP (6-((1-fluoro-3-hydroxypropan-2-yloxy)methyl)-5-methylpryrimidine-2,4 (1H,3H)-dione), ganciclovir, valganciclovir, acyclovir, valacivlovir, penciclovir, radiolabeled pyrimidine with 4-hydroxy-3-(hydroxymethyl)butyl side chain at N-1 (HHG-5-FEP) or 5-(2-)hydroxyethyl)- and 5-(3-hydroxypropyl)-substituted pyrimidine derivatives bearing 2,3-dihydroxypropyl, acyclovir-, ganciclovir- and penciclovir-like side chains for thymidine kinase; ifosfamide for oxidoreductase; 6-methoxypurine arabinoside for VZV-TK; 5-fluorocytosine for cytosine deaminase; doxorubicin for beta-glucuronidase; CB 1954 and nitrofurazone for nitroreductase; and N-(Cyanoacetyl)-L-phenylalanine, or N-(3-chloropropionyl)-L-phenylalanine for carboxypeptidase A. In some embodiments, the nucleoside agent comprises ganciclovir, valganciclovir, acyclovir, valacyclovir, or penciclovir.

In some embodiments, the vector, the cell comprising the vector, or the pharmaceutical composition provided herein can be administered before, during, or after occurrence of the disease or condition. In some embodiments, the vector, the cell comprising the vector, or the pharmaceutical composition can be used as a prophylactic and may be administered continuously to subjects. In some embodiments, the vector, the cell comprising the vector, or the pharmaceutical composition can be administered to a subject before the onset of the symptoms associated with the disease or condition.

Actual dosage levels of an agent of the disclosure (e.g., the vector, the cell comprising the vector, or the pharmaceutical composition) can be varied so as to obtain an amount of the agent to achieve the desired therapeutic response for a particular subject, composition, and mode of administration, without being toxic to the subject (e.g., the subject for immunization or the subject for treatment). The selected dosage level may depend upon a variety of pharmacokinetic factors including the activity of the particular compositions described herein, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts.

Dosage regimens may be adjusted to provide the optimum desired response (e.g., a therapeutic and/or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects (e.g., the subjects for immunization or the subjects for treatment); each unit contains a predetermined quantity of active agent calculated to produce the desired therapeutic effect in association with the required pharmaceutical carrier. The specification for the dosage unit forms of the disclosure may be determined by and directly dependent on (a) the unique characteristics of the active agent and the particular therapeutic effect to be achieved, and (b) the limitations inherent in the art of compounding such an active agent for the treatment of sensitivity in individuals. A dose may be determined by reference to a plasma concentration or a local concentration of the circular polyribonucleotide or antibody or antigen-binding fragment thereof. A dose may be determined by reference to a plasma concentration or a local concentration of the linear polyribonucleotide or antibody or antigen-binding fragment thereof.

In some embodiments, the vector, the cell comprising the vector, or the pharmaceutical composition described herein can be in a unit dosage form suitable for a single administration of a precise dosage. In unit dosage form, the formulation may be divided into unit doses containing appropriate quantities of the compositions. In unit dosage form, the formulation may be divided into unit doses containing appropriate quantities of one or more linear polyribonucleotides, antibodies or the antigen-binding fragments thereof, and/or therapeutic agents. The unit dosage may be in the form of a package containing discrete quantities of the formulation. Non-limiting examples are packaged injectables, vials, and ampoules. An aqueous suspension composition disclosed herein may be packaged in a single-dose non-reclosable container. Multiple-dose reclosable containers may be used, for example, in combination with or without a preservative. A formulation for injection disclosed herein may be present in a unit dosage form, for example, in ampoules, or in multi dose containers with a preservative.

The dosage of the vector, the cell comprising the vector, or the pharmaceutical composition lies preferably within a range of circulating concentrations that include the ED50 with little or no toxicity. The dosage may vary within this range depending upon the dosage form employed and the route of administration utilized. A therapeutically effective dose can be estimated initially from cell culture assays. A dose may be formulated in animal models to achieve a circulating plasma concentration range that includes the IC50 (i.e., the concentration of the test compound which achieves a half-maximal infection or a half-maximal inhibition) as determined in cell culture. Such information can be used to more accurately determine useful doses in humans. Levels in plasma may be measured, for example, by RT-qPCR or ddPCR methods.

An effective amount or therapeutically effective of the vector, the cell comprising the vector, or the pharmaceutical composition disclosed herein to be administered to a subject in need of treatment may be determined in a variety of ways. By way of example, the amount may be based on viral titer or efficacy in an animal model. Alternatively the dosing regimens used in clinical trials may be used as general guidelines.

In some embodiments, the daily dose may be administered in a single dose or in portions at various hours of the day. In some embodiments, a higher dosage may be required and may be reduced over time when the optimal initial response is obtained. In some embodiments, treatment may be continuous for days, weeks, or years, or may be at intervals with intervening rest periods. In some embodiments, the dosage is modified in accordance with other treatments the individual may be receiving. However, the method of treatment is in no way limited to a particular concentration or range of the retroviral particle and may be varied for each individual being treated and for each derivative used. Individualization of dosage may be required to achieve the maximum effect for a given individual. In some embodiments, the dosage administered to an individual being treated varies depending on the individual's age, severity or stage of the disease and response to the course of treatment. In some embodiments, clinical parameters for determining dosage include, but are not limited to, tumor size, alteration in the level of tumor markers used in clinical testing for particular malignancies. In some embodiments, the treating physician determines the therapeutically effective amount to be used for a given individual. In some embodiments, the therapies disclosed herein are administered as often as necessary and for the period of time judged necessary by the treating physician.

In some embodiments, multiple therapeutic courses (e.g., first and second therapeutic course) are administered to a subject in need of treatment. In some embodiments, the first and/or second therapeutic course is administered intravenously. In other embodiments, the first and/or second therapeutic course is administered via intra-arterial infusion, including but not limited to infusion through the hepatic artery, cerebral artery, coronary artery, pulmonary artery, iliac artery, celiac trunk, gastric artery, splenic artery, renal artery, gonadal artery, subclavian artery, vertebral artery, axillary artery, brachial artery, radial artery, ulnar artery, carotid artery, femoral artery, inferior mesenteric artery and/or superior mesenteric artery. Intra-arterial infusion may be accomplished using endovascular procedures, percutaneous procedures or open surgical approaches. In some embodiments, the first and second therapeutic course may be administered sequentially. In yet other embodiments, the first and second therapeutic course may be administered simultaneously. In still other embodiments, the optional third therapeutic course may be administered sequentially or simultaneously with the first and second therapeutic courses.

In some embodiments, the vector, the cell comprising the vector, or the pharmaceutical composition disclosed herein may be administered in conjunction with a sequential or concurrently administered therapeutic course(s) in high doses on a cumulative basis. For example, in some embodiments, a patient in need thereof may be systemically administered, e.g., intravenously administered, with a therapeutic course on a cumulative basis. A first therapeutic course may be systemically administered. Alternatively, the first therapeutic course may be administered in a localized manner, e.g., intra-arterially, for example a patient in need thereof may be administered via intra-arterial infusion on a cumulative basis.

In yet other embodiments, a subject in need thereof may receive a combination, either sequentially or concurrently, of systemic and intra-arterial infusions administration of high doses of the vector, the cell comprising the vector, or the pharmaceutical composition. For example, a patient in need thereof may be first systemically administered with the vector, the cell comprising the vector, or the pharmaceutical composition on a cumulative basis, followed by an additional therapeutic course of intra-arterial infusion, e.g., hepatic arterial infusion, administered delivery on a cumulative basis. In A subject in need of treatment may also be administered, either systemically or localized (for example intra-arterial infusion, such as hepatic arterial infusion) a therapeutic course of delivering the vector, the cell comprising the vector, or the pharmaceutical composition for a defined period of time. In some embodiments, the period of time may be at least one day, at least two days, at least three days, at least four days, at least five days, at least six days, at least seven days, at least one week, at least two weeks, at least three weeks, at least four weeks, at least five weeks, at least six weeks, at least seven weeks, at least eight weeks, at least 2 months, at least three months, at least four months, at least five months, at least six months, at least seven months, at least eight months, at least nine months, at least ten months, at least eleven months, at least one year, at least two years, at least three years, at least four years, or at least five years. Administration could also take place in a chronic manner, i.e., for an undefined or indefinite period of time.

Administration of the vector, the cell comprising the vector, or the pharmaceutical composition may also occur in a periodic manner, e.g., at least once a day, at least twice a day, at least three times a day, at least four times a day, at least five times a day. Periodic administration of the delivery of the vector, the cell comprising the vector, or the pharmaceutical composition may be dependent upon the time of delivery as well as the mode of administration. For example, parenteral administration may take place only once a day over an extended period of time, whereas oral administration of the delivery of the vector, the cell comprising the vector, or the pharmaceutical composition may take place more than once a day wherein administration of the delivery of the vector, the cell comprising the vector, or the pharmaceutical composition takes place over a shorter period of time.

In one embodiment, the subject is allowed to rest 1 to 2 days between the first therapeutic course and second therapeutic course. In some embodiments, the subject is allowed to rest 2 to 4 days between the first therapeutic course and second therapeutic course. In other embodiments, the subject is allowed to rest at least 2 days between the first and second therapeutic course. In yet other embodiments, the subject is allowed to rest at least 4 days between the first and second therapeutic course. In still other embodiments, the subject is allowed to rest at least 6 days between the first and second therapeutic course. In some embodiments, the subject is allowed to rest at least 1 week between the first and second therapeutic course. In yet other embodiments, the subject is allowed to rest at least 2 weeks between the first and second therapeutic course. In one embodiment, the subject is allowed to rest at least one month between the first and second therapeutic course. In some embodiments, the subject is allowed to rest at least 1-7 days between the second therapeutic course and the optional third therapeutic course. In yet other embodiments, the subject is allowed to rest at least 1-2 weeks between the second therapeutic course and the optional third therapeutic course.

In some embodiments, the vector, the cell comprising the vector, or the pharmaceutical composition is administered to increase local concentration of an interleukin (e.g., P40 or P35 of IL-12 or IL-7) and a thymidine kinase (e.g., the mutated HSV1-TK) in the cell or the microenvironment associated with the disease or condition (e.g., cancer or lesion) described herein. In some embodiments, the vector, the cell comprising the vector, or the pharmaceutical composition is administered via intra-arterial infusion, which increases local concentration of the therapeutic vector to a specific organ system. In yet other embodiments, the vector, the cell comprising the vector, or the pharmaceutical composition is administered intratumorally. Dependent upon the location of the target lesions, in some embodiments, catheterization of the hepatic artery is followed by infusion into the pancreaticoduodenal, right hepatic, and middle hepatic artery, respectively, in order to locally target hepatic lesions. In some embodiments, localized distribution to other organ systems, including the lung, gastrointestinal, brain, reproductive, splenic or other defined organ system, of the peptide or delivery vector is accomplished via catheterization or other localized delivery system. In some embodiments, intra-arterial infusions are accomplished via any other available arterial source, including but not limited to infusion through the hepatic artery, cerebral artery, coronary artery, pulmonary artery, iliac artery, celiac trunk, gastric artery, splenic artery, renal artery, gonadal artery, subclavian artery, vertebral artery, axillary artery, brachial artery, radial artery, ulnar artery, carotid artery, femoral artery, inferior mesenteric artery and/or superior mesenteric artery. In some embodiments, intra-arterial infusion is accomplished using endovascular procedures, percutaneous procedures or open surgical approaches.

Pharmaceutical Composition

Described herein is a pharmaceutical composition comprising a therapeutic agent (e.g., the vector or the cell comprising the vector described herein). In some aspects, the cell contacted with the vector described herein expresses an interleukin (e.g., P40 or P35 of IL-12 or IL-7) or a thymidine kinase (e.g., the mutated HSV1-TK) in vivo or in vitro. In some aspects, the cell is: obtained from a subject; expanded in an in vitro environment; and administer back to the subject for treating the disease or condition in the subject. In some aspects, the cell is obtained from a source that is not from the subject. In some aspects, the cell is obtained from a cell line. In some embodiments, the cell is formulated into the pharmaceutical composition. In some embodiments, the pharmaceutical composition comprises a nucleoside agent described herein.

In some aspects, the pharmaceutical composition comprises a pharmaceutically acceptable: carrier, excipient, or diluent. In some aspects, the pharmaceutical composition described herein includes at least one additional active agent other than the cell described herein. In some aspects, the at least one additional active agent is a chemotherapeutic agent, cytotoxic agent, cytokine, growth-inhibitory agent, anti-hormonal agent, anti-angiogenic agent, or checkpoint inhibitor.

In practicing the methods of treatment or use provided herein, therapeutically effective amount of pharmaceutical composition described herein is administered to a mammal having a disease or condition to be treated, e.g., cancer or lesion. In some aspects, the mammal is a human. A therapeutically effective amount may vary widely depending on the severity of the disease, the age and relative health of the subject, the potency of the therapeutic agent used and other factors. The therapeutic agents, and in some cases, compositions described herein, may be used singly or in combination with one or more therapeutic agents as components of mixtures.

The pharmaceutical composition described herein may be administered to a subject by appropriate administration routes, including but not limited to, intravenous, intraarterial, oral, parenteral, buccal, topical, transdermal, rectal, intramuscular, subcutaneous, intraosseous, transmucosal, inhalation, or intraperitoneal administration routes. The composition described herein may include, but not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

The pharmaceutical composition including a therapeutic agent may be manufactured in a conventional manner, such as, by way of example only, by means of conventional mixing, dissolving, granulating, dragee-making, levigating, emulsifying, encapsulating, entrapping or compression processes.

The pharmaceutical composition may include at least an exogenous therapeutic agent as an active ingredient in free-acid or free-base form, or in a pharmaceutically acceptable salt form. In addition, the methods and compositions described herein include the use of N-oxides (if appropriate), crystalline forms, amorphous phases, as well as active metabolites of these compounds having the same type of activity. In some aspects, therapeutic agents exist in unsolvated form or in solvated forms with pharmaceutically acceptable solvents such as water, ethanol, and the like. The solvated forms of the therapeutic agents are also considered to be disclosed herein.

In certain embodiments, the pharmaceutical composition provided herein includes one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some aspects, pharmaceutical composition described herein benefits from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, 1 about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

The pharmaceutical composition described herein can be formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In one aspect, a therapeutic agent as discussed herein, e.g., therapeutic agent is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for rehydration into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants. In some aspects, formulations suitable for subcutaneous injection also contain additives such as preserving, wetting, emulsifying, and dispensing agents. Prevention of the growth of microorganisms may be ensured by various antibacterial and antifungal agents, such as parabens, chlorobutanol, phenol, sorbic acid, and the like. In some cases, it is desirable to include isotonic agents, such as sugars, sodium chloride, and the like. Prolonged absorption of the injectable pharmaceutical form may be brought about by the use of agents delaying absorption, such as aluminum monostearate and gelatin.

For intravenous injections or drips or infusions, a pharmaceutical composition described herein is formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections may involve bolus injection or continuous infusion. Pharmaceutical composition for injection may be presented in unit dosage form, e.g., in ampoules or in multi dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

For administration by inhalation, a therapeutic agent is formulated for use as an aerosol, a mist or a powder. Pharmaceutical compositions described herein are conveniently delivered in the form of an aerosol spray presentation from pressurized packs or nebulizers, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the therapeutic agent described herein and a suitable powder base such as lactose or starch. Formulations that include a composition are prepared as solutions in saline, employing benzyl alcohol or other suitable preservatives, fluorocarbons, and/or other solubilizing or dispersing agents known in the art. Preferably these compositions and formulations are prepared with suitable nontoxic pharmaceutically acceptable ingredients. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

In another aspect, dosage forms include microencapsulated formulations. In some aspects, one or more other compatible materials are present in the microencapsulation material. Non-limiting example of materials includes pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Liquid formulation dosage forms for oral administration are optionally aqueous suspensions selected from the group including, but not limited to, pharmaceutically acceptable aqueous oral dispersions, emulsions, solutions, elixirs, gels, and syrups. In addition to therapeutic agent the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some aspects, the aqueous dispersions further include a crystal-forming inhibitor.

In some aspects, the pharmaceutical composition described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some aspects, SEDDS provides improvements in the bioavailability of hydrophobic active ingredients.

Buccal formulations are administered using a variety of formulations known in the art. In addition, the buccal dosage forms described herein may further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

For intravenous injections, a pharmaceutical composition is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some aspects, a composition described herein is in a form suitable for parenteral injection as a sterile suspensions, solutions or emulsions in oily or aqueous vehicles, and contain formulatory agents such as suspending, stabilizing and/or dispersing agents. The compositions for parenteral administration include aqueous solutions of an agent that modulates the activity of a carotid body in water soluble form. Additionally, suspensions of an agent that modulates the activity of a carotid body are optionally prepared as appropriate, e.g., oily injection suspensions.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some aspects, the pharmaceutical composition can be provided that include particles of a therapeutic agent and at least one dispersing agent or suspending agent for oral administration to a subject. The formulations may be a powder and/or granule for suspension, and upon admixture with water, a substantially uniform suspension is obtained.

Furthermore, the pharmaceutical composition optionally includes one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, the pharmaceutical composition optionally includes one or more salts in an amount required to bring osmolality of the pharmaceutical composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite, and ammonium sulfate.

In one embodiment, the aqueous suspensions and dispersions described herein remain in a homogenous state for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

An aerosol formulation for nasal administration is generally an aqueous solution designed to be administered to the nasal passages in drops or sprays. Nasal solutions may be similar to nasal secretions in that they are generally isotonic and slightly buffered to maintain a pH of about 5.5 to about 6.5, although pH values outside of this range may additionally be used. Antimicrobial agents or preservatives may also be included in the formulation.

An aerosol formulation for inhalations and inhalants may be designed so that the agent or combination of agents is carried into the respiratory tree of the subject when administered by the nasal or oral respiratory route. Inhalation solutions may be administered, for example, by a nebulizer. Inhalations or insufflations, comprising finely powdered or liquid drugs, may be delivered to the respiratory system as a pharmaceutical aerosol of a solution or suspension of the agent or combination of agents in a propellant, e.g., to aid in disbursement. Propellants may be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers. Aerosol formulations may also include other components, for example, ethanol, isopropanol, propylene glycol, as well as surfactants or other components such as oils and detergents. These components may serve to stabilize the formulation and/or lubricate valve components.

Kit

Described herein, in some aspects, are kits for using the vector described herein. In some embodiments, the kit can be used to treat a disease or condition in a subject. In some aspects, the kit comprises an assemblage of materials or components apart from the vector or a cell comprising the vector. In some aspects, the kit comprises the components for assaying the number of units of a biomolecule (e.g., a therapeutic agent including the vector, the cell, IL-12 or IL-7, the mutant HSV1-TK, or a combination thereof) synthesized, and/or released or expressed by the cell described herein. In some aspects, the kit comprises components for performing assays such as enzyme-linked immunosorbent assay (ELISA), single-molecular array (Simoa), PCR, and qPCR. The exact nature of the components configured in the kit depends on its intended purpose. For example, kits can be configured for the purpose of treating a disease or condition disclosed herein (e.g., cancer or lesion) in a subject. In some aspects, the kit is configured particularly for the purpose of treating mammalian subjects. In some aspects, the kit is configured particularly for the purpose of treating human subjects.

Instructions for use may be included in the kit. In some aspects, the kit comprises instructions for administering the vector, the cell, or the pharmaceutical composition described herein to a subject in need thereof. In some aspects, the kit comprises instructions for further engineering the vector or cell to express a biomolecule (e.g., a therapeutic agent including the IL-12 or IL-7 and the mutant HSV1-TK). In some aspects, the kit comprises instructions thawing or otherwise restoring biological activity of the cell, which may have been preserved during storage or transportation. In some aspects, the kit comprises instructions for measure viability of the preserved cell, to ensure efficacy for its intended purpose (e.g., therapeutic efficacy if used for treating a subject).

Optionally, the kit also contains other useful components, such as, diluents, buffers, pharmaceutically acceptable carriers, syringes, catheters, applicators, pipetting or measuring tools, bandaging materials or other useful paraphernalia. The materials or components assembled in the kit may be provided to the practitioner stored in any convenient and suitable ways that preserve their operability and utility. For example, the components may be in dissolved, dehydrated, or lyophilized form; they may be provided at room, refrigerated or frozen temperatures. The components are typically contained in suitable packaging material.

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, "or" may refer to "and", "or," or "and/or" and may be used both exclusively and inclusively. For example, the term "A or B" may refer to "A or B", "A but not B", "B but not A", and "A and B". In some cases, context may dictate a particular meaning.

Any systems, methods, software, and platforms described herein are modular. Accordingly, terms such as "first" and "second" do not necessarily imply priority, order of importance, or order of acts.

The term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to ±10% of a stated number or value.

The terms "increased", "increasing", or "increase" are used herein to generally mean an increase by a statically significant amount. In some aspects, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms "decreased", "decreasing", or "decrease" are used herein generally to mean a decrease by a statistically significant amount. In some aspects, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

As used herein, "nucleic acid" refers to a polynucleotide containing at least two covalently linked nucleotide or nucleotide analog subunits. A nucleic acid is generally a deoxyribonucleic acid (DNA), a ribonucleic acid (RNA), or an analog of DNA or RNA. The nucleic acid is generally single-stranded, double-stranded, or a mixture thereof. For purposes herein, unless specified otherwise, the nucleic acid is double-stranded, or it is apparent from the context.

As used herein, "DNA" is meant to include all types and sizes of DNA molecules including cDNA, plasmids and DNA including modified nucleotides and nucleotide analogs.

As used herein, "nucleotides" include nucleoside mono-, di-, and triphosphates. Nucleotides also include modified nucleotides, such as, but are not limited to, phosphorothioate nucleotides and deazapurine nucleotides and other nucleotide analogs.

The term "polynucleotide" as used herein means a polymeric form of nucleotide of any length, and includes ribonucleotides and deoxyribonucleotides. Such term also includes single- and double-stranded DNA, as well as single- and double-stranded RNA. The term also includes modified polynucleotides such as methylated or capped polynucleotides.

As used herein, the term "subject" refers to animals, plants, insects, and birds into which the large DNA molecules are introduced. Included are higher organisms, such as mammals and birds, including humans, primates, rodents, cattle, pigs, rabbits, goats, sheep, mice, rats, guinea pigs, cats, dogs, horses, chicken and others. Subject may or may not have a disease or condition.

As used herein, "administering to a subject" is a procedure by which one or more delivery agents and/or large nucleic acid molecules, together or separately, are introduced into or applied onto a subject such that target cells which are present in the subject are eventually contacted with the agent and/or the large nucleic acid molecules.

As used herein, "delivery vector" or "delivery vehicle" or "therapeutic vector" or "therapeutic system" refers to both viral and non-viral particles that harbor and transport exogenous nucleic acid molecules to a target cell or tissue. Viral vehicles include, but are not limited to, retroviruses, adenoviruses, lentiviral viruses, herpes viruses and adeno-associated viruses. Non-viral vehicles include, but are not limited to, microparticles, nanoparticles, virosomes and liposomes. "Targeted," as used herein, refers to the use of ligands that are associated with the delivery vehicle and target the vehicle to a cell or tissue. Ligands include, but are not limited to, antibodies, receptors and collagen-binding domains.

As used herein, "delivery," which is used interchangeably with "transduction," refers to the process by which exogenous nucleic acid molecules are transferred into a cell such that they are located inside the cell. Delivery of nucleic acids is a distinct process from expression of nucleic acids.

As used herein, "expression" refers to the process by which nucleic acid is translated into peptides or is transcribed into RNA, which, for example, can be translated into peptides, polypeptides or proteins. If the nucleic acid is derived from genomic DNA, expression includes, if an appropriate eukaryotic host cell or organism is selected, splicing of the mRNA. For heterologous nucleic acid to be expressed in a host cell, it must initially be delivered into the cell and then, once in the cell, ultimately reside in the nucleus.

As used herein, a "therapeutic course" refers to the periodic or timed administration of the vectors disclosed herein within a defined period of time. Such a period of time is at least one day, at least two days, at least three days, at least five days, at least one week, at least two weeks, at least three weeks, at least one month, at least two months, or at least six months. Administration could also take place in a chronic manner, i.e., for an undefined period of time. The periodic or timed administration includes once a day, twice a day, three times a day or other set timed administration.

As used herein, the terms "co-administration," "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments, a therapeutic agent as disclosed in the present application will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, a therapeutic agent and the other agent(s) are administered in a single composition. In some embodiments, a therapeutic agent and the other agent(s) are admixed in the composition. In further embodiments, a therapeutic agent and the other agent(s) are administered at separate times in separate doses.

As used herein, the term "mutant thymidine kinase" refers to not only the specific protein described herein (as well as the nucleic acid sequences which encode these proteins), but derivatives thereof which may include various structural forms of the primary protein which retain biological activity.

As used herein, the term "mutated" or "replaced by another nucleotide" means a nucleotide at a certain position is replaced at that position by a nucleotide other than that which occurs in the unmutated or previously mutated sequence. That is, in some instances, specific modifications may be made in different nucleotides. In some embodiments, the replacements are made such that the relevant splice donor and/or acceptor sites are no longer present in a gene.

As used herein, a "polar amino acid" refers to amino acid residues Asn (N), Cys (C), Gln (Q), Gly (G), Ser (S), Thr (T) or Tyr (Y).

As used herein, a "non-polar amino acid" refers to amino acid residues Ala (A), Ile (I), Leu (L), Met (M), Phe (F), Pro (P), Trp (W), or Val (V).

As used herein, a "basic amino acid" refers to amino acid residues Arg (R), His (H), or Lys (K).

As used herein, an "acidic amino acid" refers to amino acid residues Asp (D) or Glu (E).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

The following illustrative examples are representative of embodiments of the stimulation, systems, and methods described herein and are not meant to be limiting in any way.

Example 1. Generation of Mouse IL-12 and Human IL-12 Vector

Generation of Mouse IL-12 Vector

Figure 1:
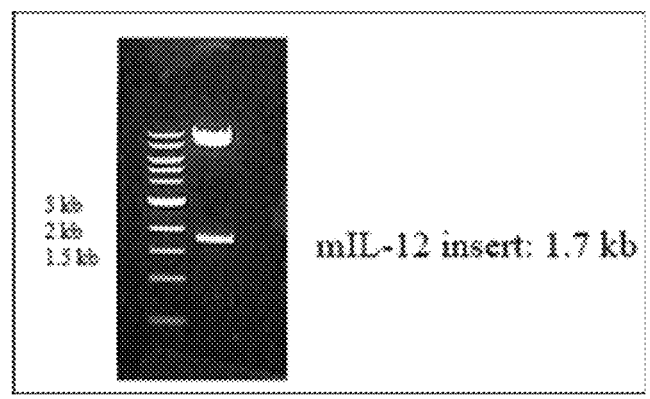
FIG. 1 illustrates mouse IL-12 (mIL-12) gene insert in a payload vector described herein.

The mouse IL-12 (mIL-12) was first engineered into a vector as shown in FIG. 1 (mouse_IL-12, 1740 bp; AgeI_Start_P40_Furin site_GSG_T2A_Start_P35_HIS_Stop_BamHI).

P40 and P35 (peptide sequences as showing in Table 1) were linked by T2A linker (GSGEGRGSLLTCGDVEEN-PGP) in the payload vector. In order to increase the protein expression by assuring the cleavage between P40 and P35, a furin site (RRKR) followed by the amino acids, GSG were added at the end of P40 subunit (FIG. 2). This would create a P40 protein with additional two amino acids (RR) only at the end of the protein sequence instead of extra 23 amino acids without the furin site. A HIS tag was added after P35 for a detection as well. The mIL-12 gene was synthesized in Genscript (Piscataway, NJ), amplified, and inserted at AgeI and BamHI site into the payload vector (FIG. 2).

TABLE 1

Mouse IL-12 sequence in the payload

```
Mouse IL12 P40 sunbunit-MCPQKLTISW FAIVLLVSPL MAMWELEKDV YVVEVDWTPD APGETVNLTC
DTPEEDDITW TSDQRHGVIG SGKTLTITVK EFLDAGQYTC HKGGETLSHS HLLLHKKENG IWSTEILKNF
KNKTFLKCEA PNYSGRFTCS WLVQRNMDLK FNIKSSSSSP DSRAVTCGMA SLSAEKVTLD QRDYEKYSVS
CQEDVTCPTA EETLPIELAL EARQQNKYEN YSTSFFIRDI IKPDPPKNLQ MKPLKNSQVE VSWEYPDSWS
TPHSYFSLKF FVRIQRKKEK MKETEEGCNQ KGAFLVEKTS TEVQCKGGNV CVQAQDRYYN
SSCSKWACVP CRVRS Mouse IL12 P35 subunit-MCQSRYLLFL ATLALLNHLS LARVIRVIPV SGPARCLSQS RNLLKTTDDM
VKTAREKLKH YSCTAEDIDH EDITRDQTST LKTCLPLELH KNESCLATRE TSSTTRGSCL PPQKTSLMMT
LCLGSIYEDL KMYQTEFQAI NAALQNHNHQ QIILDKGMLV AIDELMQSLN HNGETLRQKP
PVGEADPYRV KMKLCILLHA FSTRVVTINR VMGYLSSA
```

Figure 4:
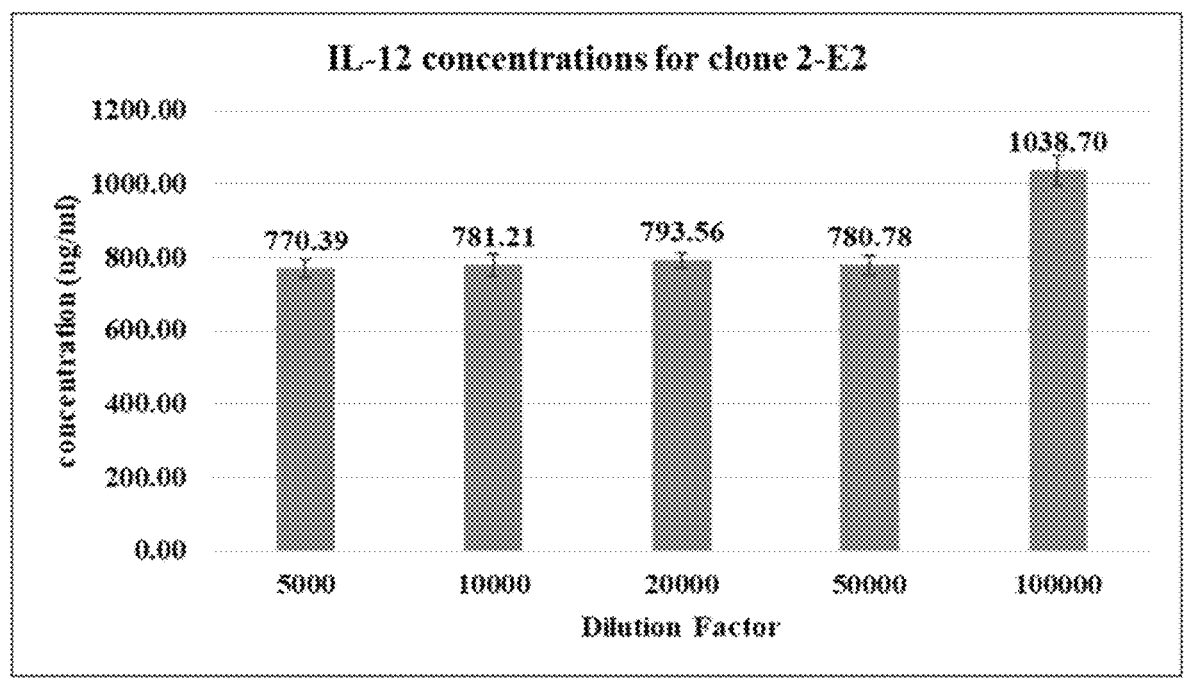
FIG. 4 illustrates mIL-12 expression by ELISA.

A375 melanoma testing cell line was transduced with the mIL-12 vector (e.g., a retroviral vector) and cloned as a single clonal cell line. Expression of secreted proteins from clonal cell lines were tested by mIL-12 ELISA and Western Blotting (FIG. 3). The reduced sample clearly showed two subunits, P40 and P35, whereas the non-reducing sample showed a protein size of 70 kDa in the Western blot, indicating the presence of heterodimer comprising the P40 and P35. The conditioned media (CM) from A375 cells transduced with the mIL-12 retroviral vector were used to quantify the amount of secreted mIL-12 by ELISA. The clone 2-E2 was picked for further in vitro studies (FIG. 4).

Generation of Human IL-12 Vector

Human IL-12 (Table 2) was also engineered into a retroviral vector as follows: Human_IL-12, 1740 bp; AgeI_Kozak_Start_P40_Furin site_GSG_T2A_Start_P35_Stop_BamHI. For human IL-12, the same engineering method as in generation of the mIL-12 was applied except for the HIS tag. The HIS tag was removed in the hIL-12 gene.

TABLE 2

Human IL-12 sequence in the payload

```
Human IL-12 P40 subunit-MCHQQLVISW FSLSFLASPL VAIWELKKDV YVVELDWYPD APGEMVVLTC
DTPEEDGITW TLDQSSEVLG SGKTLTIQVK EFGDAGQYTC HKGGEVLSHS LLLLHKKEDG IWSTDILKDQ
KEPKNKTFLR CEAKNYSGRF TCWWLTTIST DLTFSVKSSR GSSDPQGVTC GAATLSAERV RGDNKEYEYS
VECQEDSACP AAEESLPIEV MVDAVHKLKY ENYTSSFFIR DIIKPDPPKN LQLKPLKNSR QVEVSWEYPD
TWSTPHSYFS LTFCVQVQGK SKREKKDRVF TDKTSATVIC RKNASISVRA QDRYYSSSWS EWASVPCS Human IL-12 P35 subunit-MCPARSLLLV ATLVLLDHLS LARNLPVATP DPGMFPCLHH SQNLLRAVSN
MLQKARQTLE FYPCTSEEID HEDITKDKTS TVEACLPLEL TKNESCLNSR ETSFITNGSC LASRKTSFMM
ALCLSSIYED LKMYQVEFKT MNAKLLMDPK RQIFLDQNML AVIDELMQAL NFNSETVPQK SSLEEPDFYK
TKIKLCILLH AFRIRAVTID RVMSYLNAS
```

P40 and P35 (peptide sequences as showing in Table 2) were linked by T2A linker (GSGEGRGSLLTCGDVEENPGP) in the payload vector. In order to increase the protein expression by assuring the cleavage between P40 and P35, a furin site (RRKR) followed by the amino acids, GSG were added at the end of P40 subunit (FIG. 2). This would create a P40 protein with additional two amino acids (RR) only at the end of the protein sequence instead of extra 23 amino acids without the furin site. The hIL-12 gene was synthesized in Genscript (Piscataway, NJ), amplified, and inserted at AgeI and BamHI site into the payload vector.

Efficacy of mIL-12 In Vitro

Figure 5:
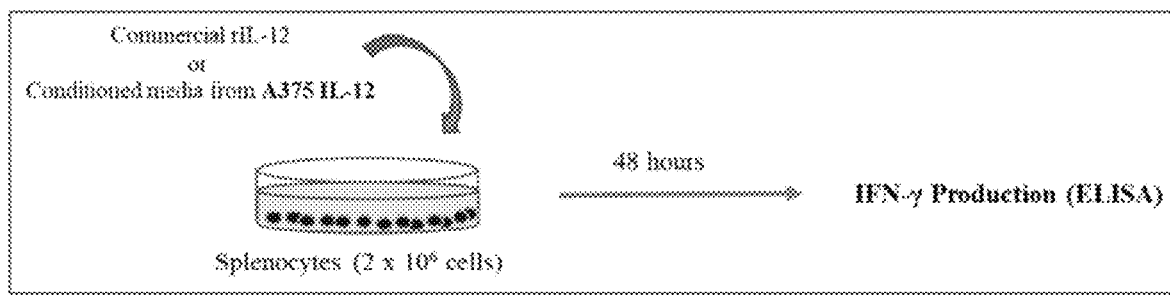
FIG. 5 illustrates experimental set-up for testing IFN-γ production from stimulation with commercial rIL-12 vs. the conditioned media (CM) of mIL-12 expressing A375 cells.
Figure 6:
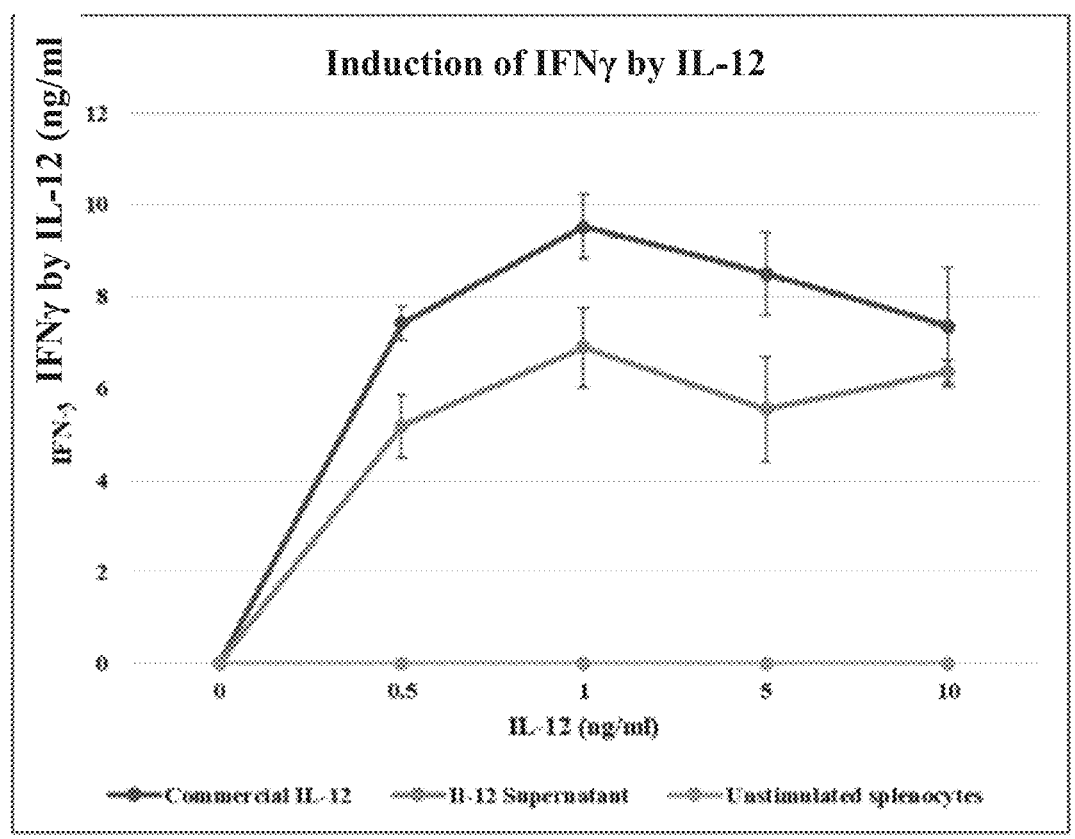
FIG. 6 illustrates results of IFN-γ ELISA at various amounts of IL-12 for stimulation.

Functionality of mIL-12 was examined by incubating mouse splenocytes with mIL-12 and measuring INF-γ. About $2\times10^6$ mouse splenocytes were stimulated with either commercial recombinant mouse IL-12 (rIL-12) or the CM from mIL-12 retroviral vector transduced and stably expressing A375 cells for 48 hours. Following stimulation, the CM from each culture was collected and measured for IFN-γ production by ELISA (FIG. 5). The results showed that the CM from the mIL-12 stably expressing A375 cells induced mouse INF-γ production in mouse splenocytes in a dose dependent manner and it was as effective as the rIL-12 (FIG. 6).

Figure 7:
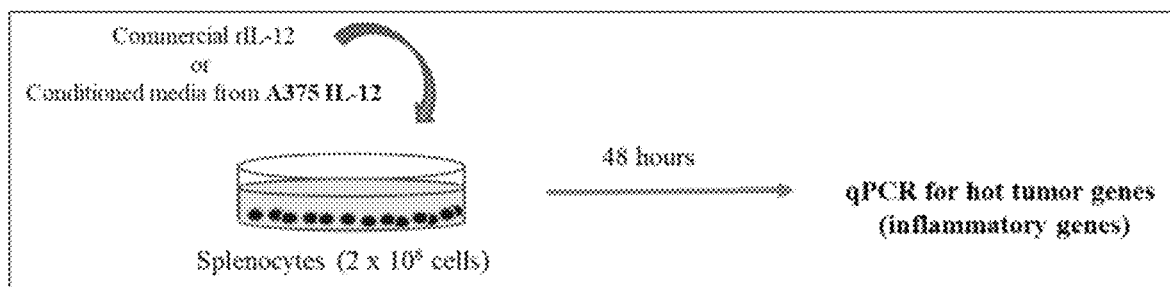
FIG. 7 illustrates experimental set-up for testing hot tumor gene expression after stimulating splenocytes with commercial rIL-12 vs. the CM of mIL-12 expressing A375 cells.
Figure 8:
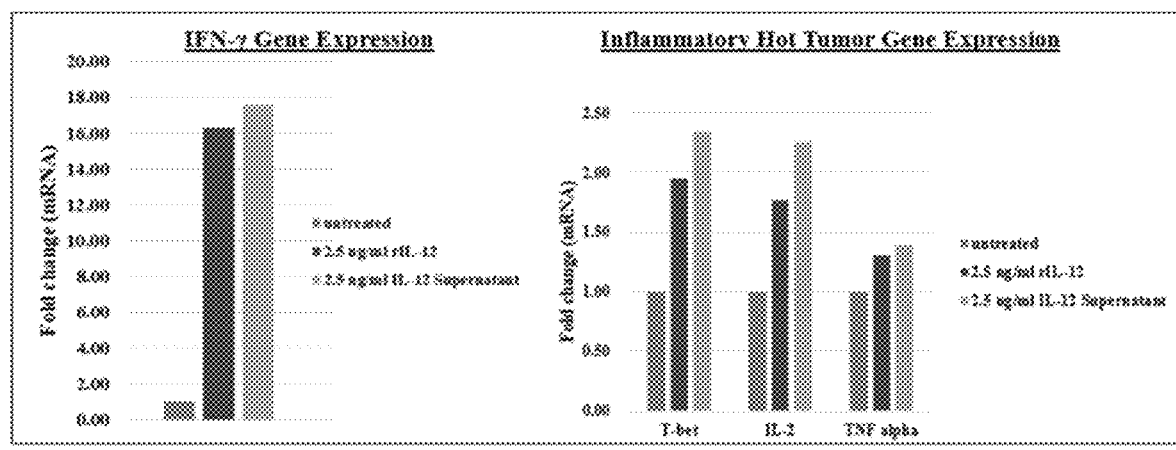
FIG. 8 illustrates IFN-γ and inflammatory hot tumor gene expression after stimulating splenocytes with commercial rIL-12 and the CM of mIL-12 expressing A375 cells.

Activation of inflammatory genes from immune cells with the mIL-12 stably expressing A375 cells were further evaluated. About $2\times10^6$ mouse splenocytes were stimulated with either commercial rIL-12 or the CM from the mIL-12 stably expressing A375 at the concentration of IL-12 at 2 ng/mL for 48 hours. Following stimulation, the cells from each group were collected and analyzed for the expression of inflammatory genes via qPCR. The results demonstrated that the CM from the mIL-12 stably expressing A375 induced IFN-γ and other inflammatory genes just as effectively as commercial rIL-12 (FIG. 7 and FIG. 8).

Figure 9:
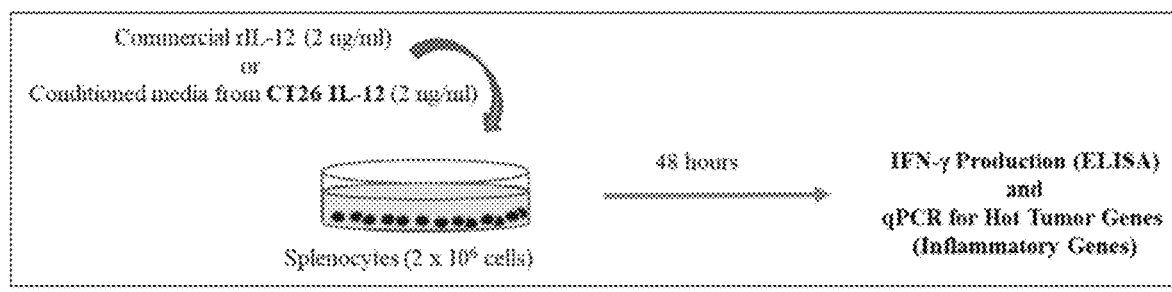
FIG. 9 illustrates experimental set-up for testing IFN-γ production and hot tumor gene expression after stimulating splenocytes with commercial rIL-12 vs. the CM of mIL-12 expressing CT26 cells.
Figure 10:
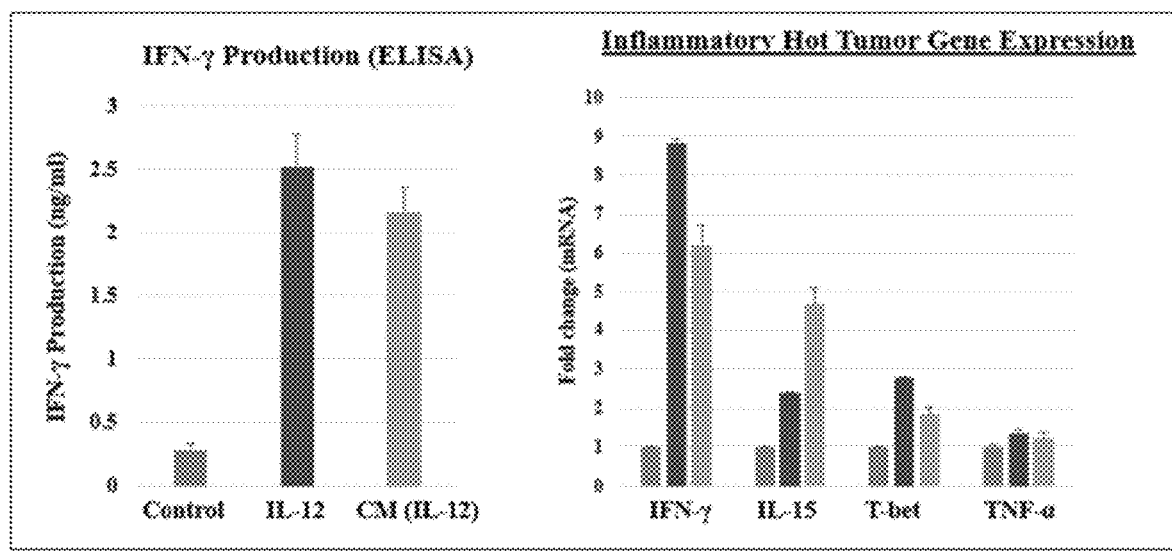
FIG. 10 illustrates IFN-γ and inflammatory hot tumor gene expression after stimulating splenocytes with commercial rIL-12 and the CM of mIL-12 expressing CT26 cells.
Figure 11:
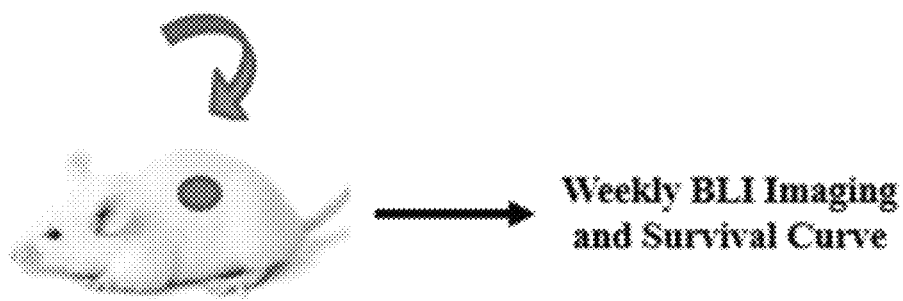
FIG. 11 illustrates mouse cartoon of subcutaneous implantation of CT26 cells expressing either luciferase gene alone or luciferase and mIL-12 gene.
Figure 12:
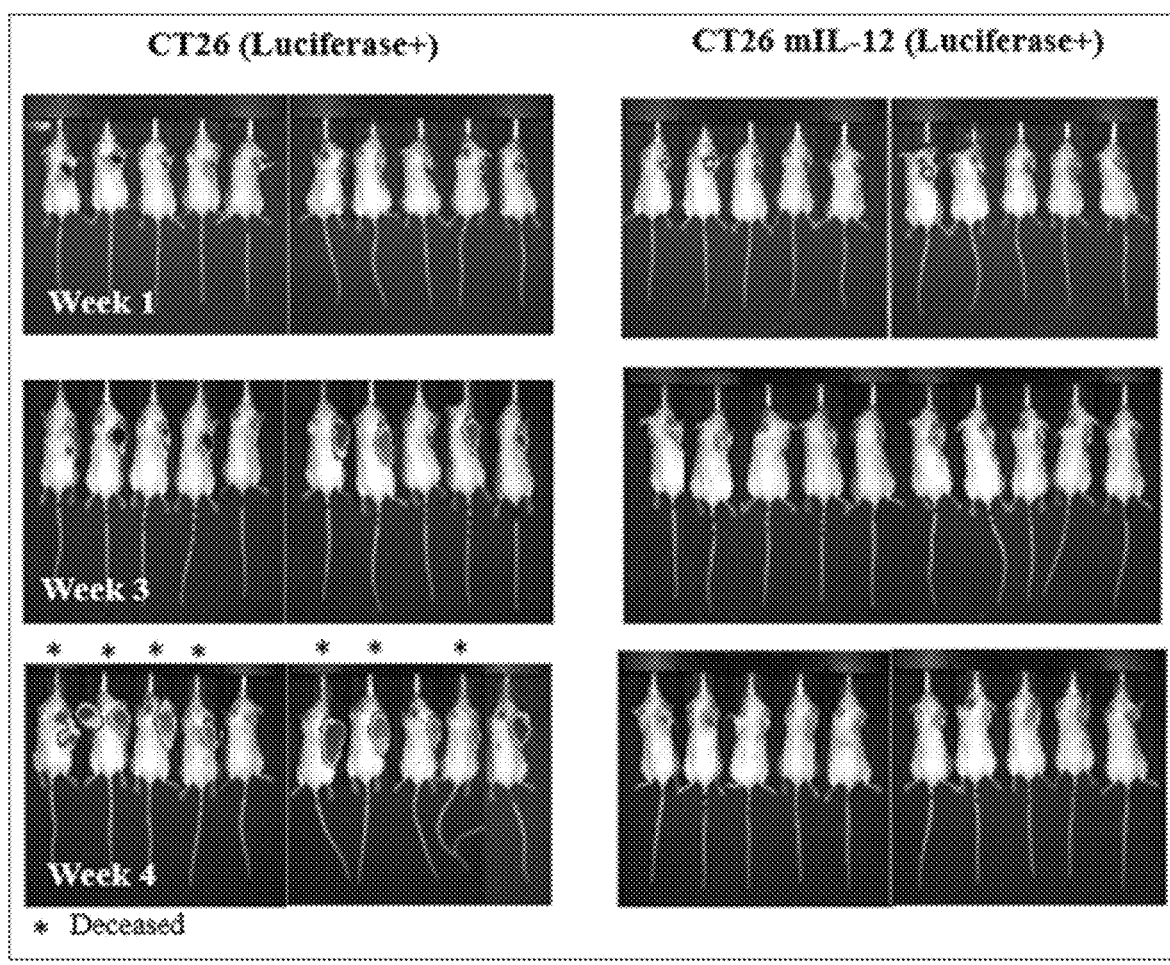
FIG. 12 illustrates bio-luminescence images of animals with implanted CT26 tumor cells
Figure 13:
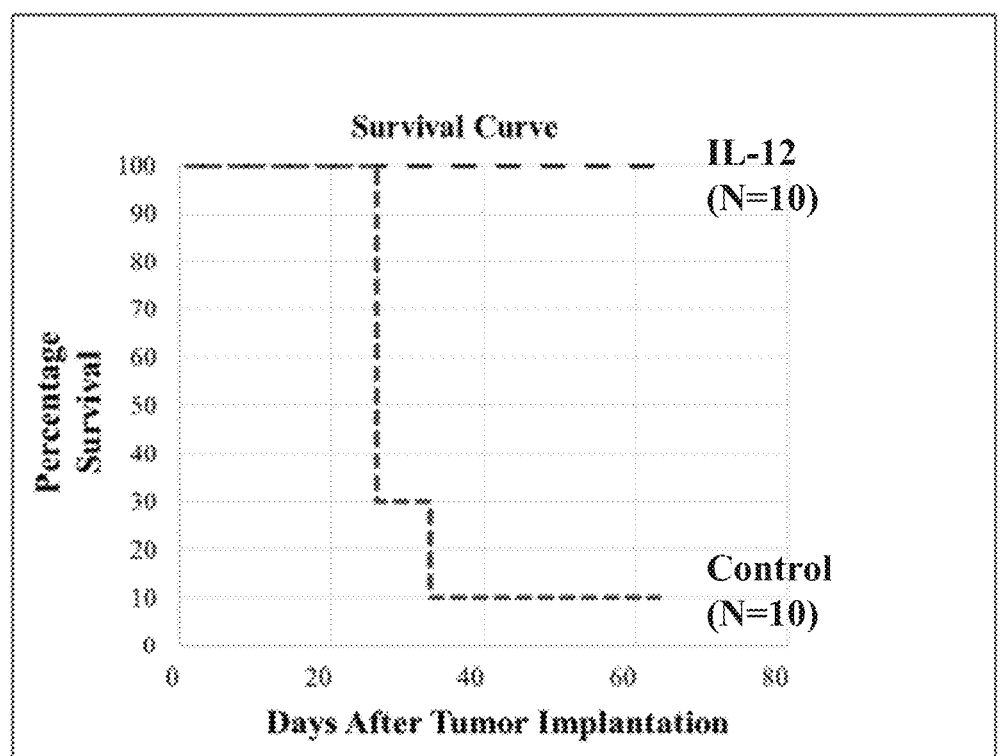
FIG. 13 illustrates survival curves of animals implanted with CT26 cells expressing mIL-12 or control.

Next, CT26, murine colorectal carcinoma cell line was transduced with the mIL-12 retroviral vector and examined whether or not secreted mIL-12 can produce IFN-γ and activate inflammatory genes from immune cells. About $2\times10^6$ mouse splenocytes were stimulated with either commercial rIL-12 or the CM from mIL-12 expressing CT26 cells at the concentration of 2 ng/mL for 48 hours. Following stimulation, the supernatant and cells from each group were collected and analyzed for the production of IFN-γ via ELISA and the expression of inflammatory genes via qPCR. The results showed that the CM from mIL-12 expressing CT26 cells induced IFN-γ production and other inflammatory genes just as effectively as commercial rIL-12 (FIG. 9 and FIG. 10). Some preliminary animal studies were performed by implanting $1.5\times10^5$ CT26 cells stably expressing luciferase gene or CT26 cells stably expressing luciferase and mIL-12 gene from the retroviral vector cells into the right shoulder flank. For the continuous in vivo monitoring of luciferase expressing CT26 tumor in the shoulder flank, an IVIS imaging system was used (FIG. 11). Bio-luminescence images of animals implanted with either CT26 expressing luciferase or luciferase and mIL-12 tumor cells are shown in FIG. 12. Before in vivo imaging, animals bearing tumors received 200 μL of luciferin (15 mg/mL). The survival curves present a 100% survival rate up to 63 days until the end of the study with CT26 expressing mIL-12 whereas only one animal survived in the control group (FIG. 13).

Figure 14:
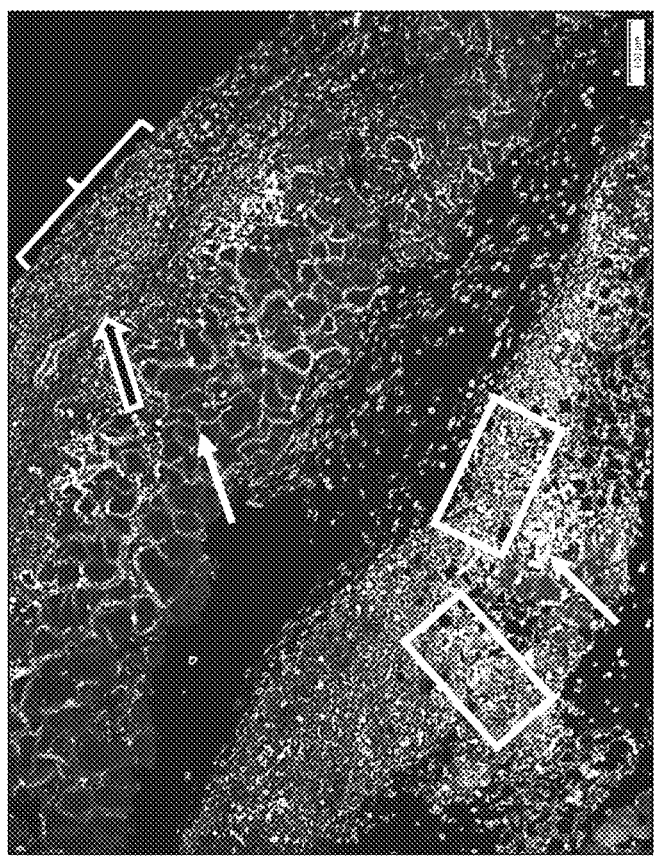
FIG. 14 illustrates anti-CD8 and anti-CD11b staining in background of Dapi-blue staining of cellular DNA of control and mIL-12 expressing tumor tissues. As indicated in the figure legends, arrows indicate localizations of anti-CD8 and anti-CD11b staining, and brackets indicate regions that are dominated by Dapi-blue staining (indicating cells lacking staining signal from either anti-CD8 or anti-CD11b). As the greyscale representations of the three-color microscopy images makes clear, the CT26 tumor tissue that express mIL-12 show a high degree of infiltration by CD8+ cytotoxic T-cells and CD11b+ myeloid cells that is absent in the control CT26 tumor tissue lacking mIL-12 expression. Isolated cells expressing CD8 and CD11b are observed in the control tissue, whereas these populations of cells are dramatically enriched in the mIL-12-expressing tissue.
Figure 14:
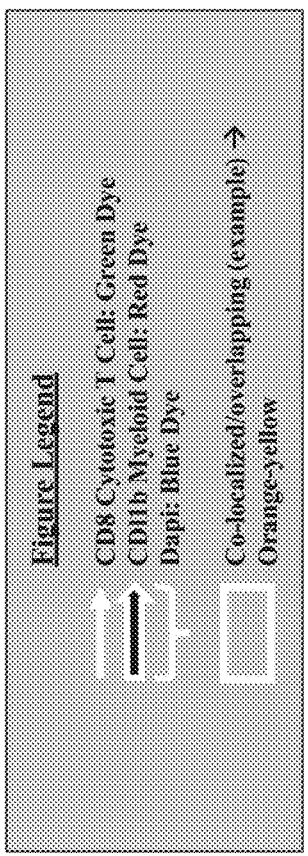
Figure 14:
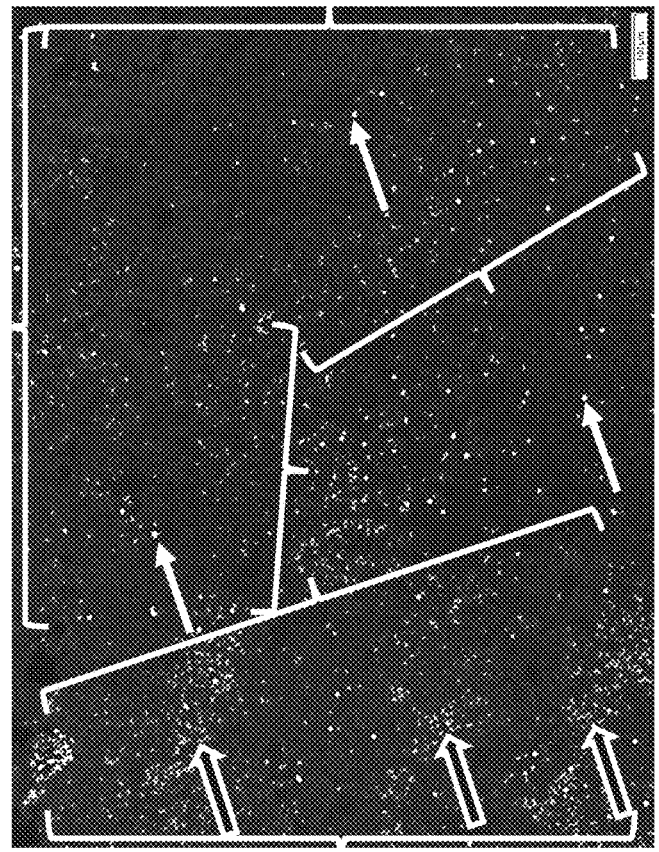
Figure 15:
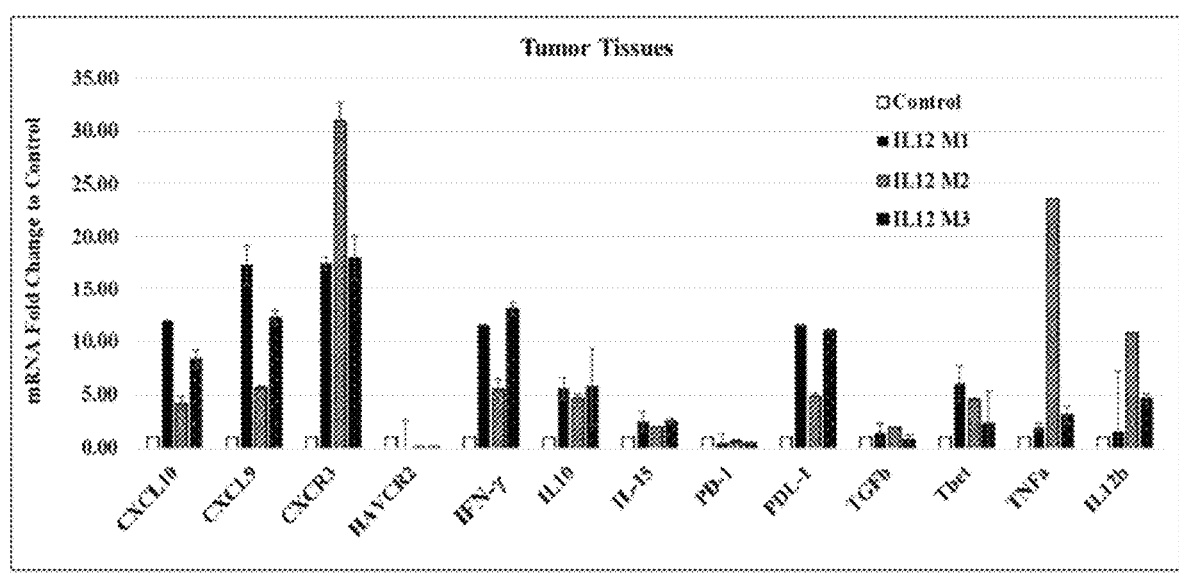
FIG. 15 illustrates expression of inflammatory hot tumor genes from the tumor tissues expressing mIL-12.
Figure 16:
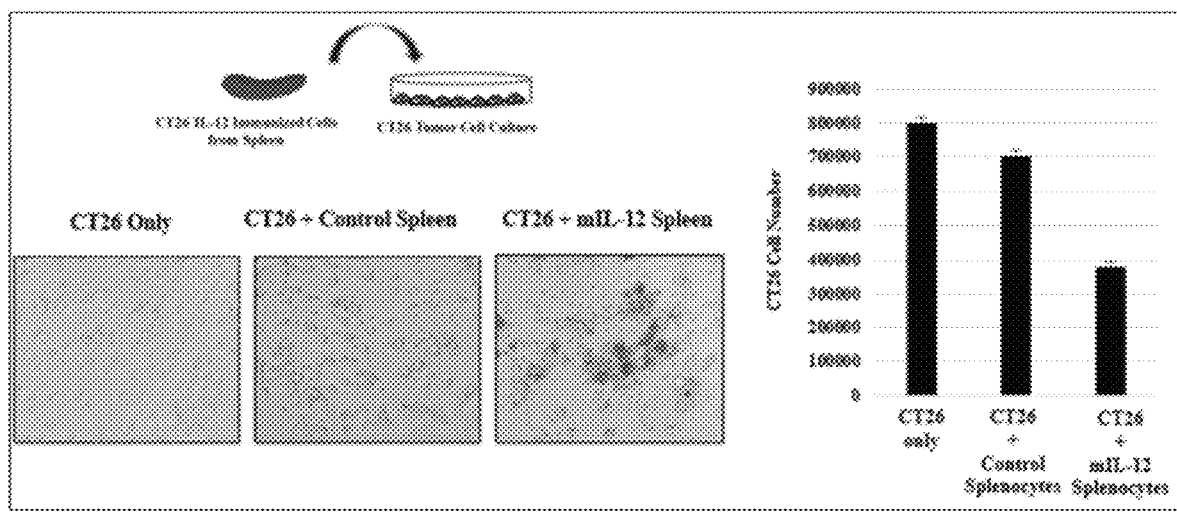
FIG. 16 illustrates viable cell count of CT26 cells after incubation with splenocytes extracted from control or CT26 expressing mIL-12 recipient group.
Figure 17:
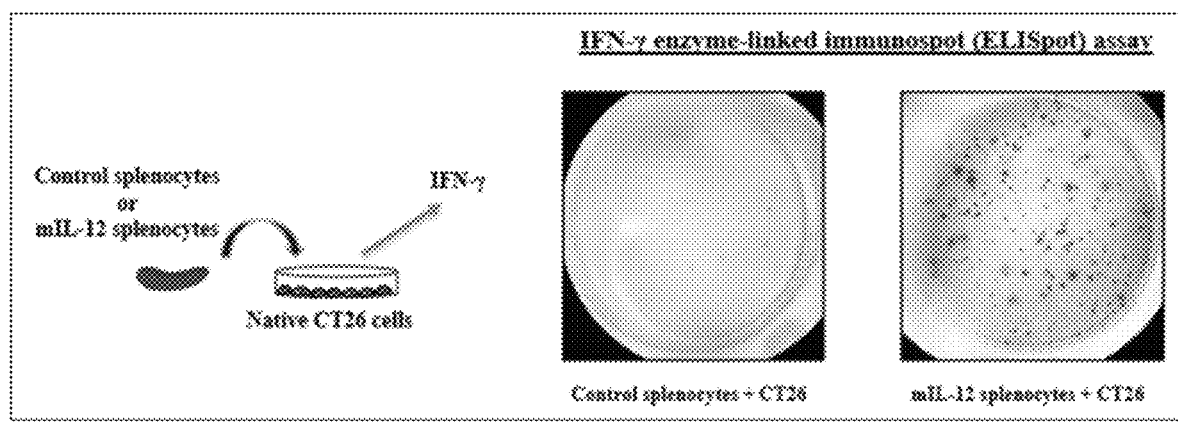
FIG. 17 illustrates IFN-γ Enzyme-Linked Immunospot (ELISpot) assay with control or mIL-12 splenocytes.

Some CT26 tumor tissues were extracted from control and mIL-12 groups and stained for presence of CD8 (cytotoxic T cell) and CD11b (myeloid) (FIG. 14). Increased CD8 and CD11b positive immune cells were detected in the CT26 expressing mIL-12 tumor tissue. CT26 tumor tissues from control and mIL-12 groups were collected and analyzed for the expression of multiple inflammatory hot tumor genes, including T cell attracting chemokines CXCL9 and CXCL10 via qPCR (FIG. 15). The tumor tissues from three individual CT26 expressing mIL-12 recipients were compared to control. About $5\times10^5$ splenocytes from either control or CT26 expressing mIL-12 recipient group were mixed with $5\times10^4$ native CT26 cells for 72 hours and counted for viable CT26 cells. Data indicated that mIL-12 splenocytes could more effectively kill CT26 target cells as shown in the cell pictures of light microscopy (FIG. 16). The IFN-γ enzyme-linked immunospot (ELISpot) assay is an immunoassay that measures the frequency of IFN-γ secreting cells at the single-cell level. In this assay, immune cells are cultured on a surface coated with a specific IFN-γ capture antibody in the presence of stimuli (etc., antigen, cancer cells). To perform this assay, about $3\times10^5$ splenocytes from either control or CT26 expressing mIL-12 immunized animal were mixed with $1\times10^5$ native CT26 cancer cells (target stimuli) for 24 hours. Each spot corresponds to an individual cytokine-secreting cell (FIG. 17). mIL-12 retroviral vectors transduced both A375 and CT26 cells with high levels of mIL-12. Secreted mIL-12 was as functionally effective as commercial IL-12 in inducing T-cell activation and promoting IFN-γ production in vitro.

mIL-12 Promoted Survival of Tumor Bearing Animals (100% of CT26 Expressing mIL-12 Tumor Bearing Animals).

Increased infiltration of immune cells and upregulated expression of inflammatory hot tumor genes were observed in CT26 expressing mIL-12 tumor tissues. Peripheral immune cells from CT26 expressing mIL-12 animals could effectively kill native CT26 tumor cells in vitro as well.

Example 2. P35 Subunit and P70 Expression

Interleukin-12 (IL-12) is a heterodimeric pro-inflammatory cytokine that regulates T-cell and natural killer-cell responses, induces the production of interferon-γ (IFN-γ), favors the differentiation of T helper 1 (TH1) cells, and is an important link between innate resistance and adaptive immunity. While IL-12 has been shown to be therapeutically effective for treating certain diseases or conditions (e.g., cancer), systematic administration of IL-12 has been shown to be toxic.

Figure 18A:
FIG. 18A illustrates an exemplary retroviral vector encoding P35 subunit of human IL-12.
Figure 18B:
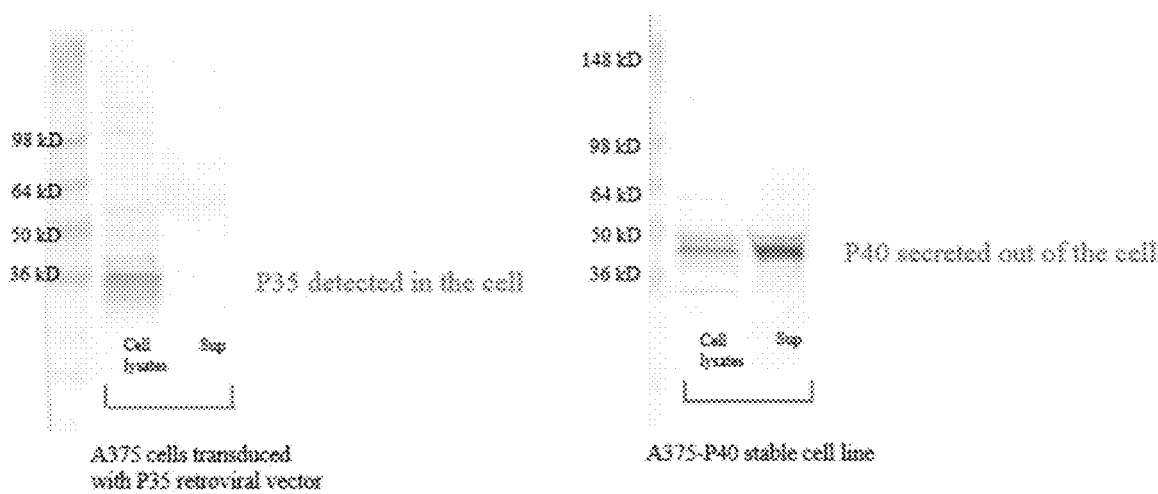
FIG. 18B illustrates Western blotting showing: expression of P35 in A375 cells transduced with a retroviral vector described herein for encoding and expressing the P35 subunit of IL-12 (left); and expression and secretion of P40 subunit by A375 cells stably expressing P40 subunit.

To decrease IL-12 toxicity for therapeutic purposes, a retroviral vector was designed to encode and express P35 subunit only. FIG. 18A illustrates an exemplary retroviral vector encoding P35 subunit of IL-12. The expression of the P35 subunit mediated by the retroviral vector can modulate the expression of IL-12 and thus modulate the toxicity associated with IL-12. FIG. 18B illustrates Western blots showing: expression of P35 in A375 cells transduced with a retroviral vector described herein for encoding and expressing the P35 subunit of IL-12 (left); and expression and secretion of P40 subunit by A375 cells (A375-P40 stable cell line).

Figure 19:
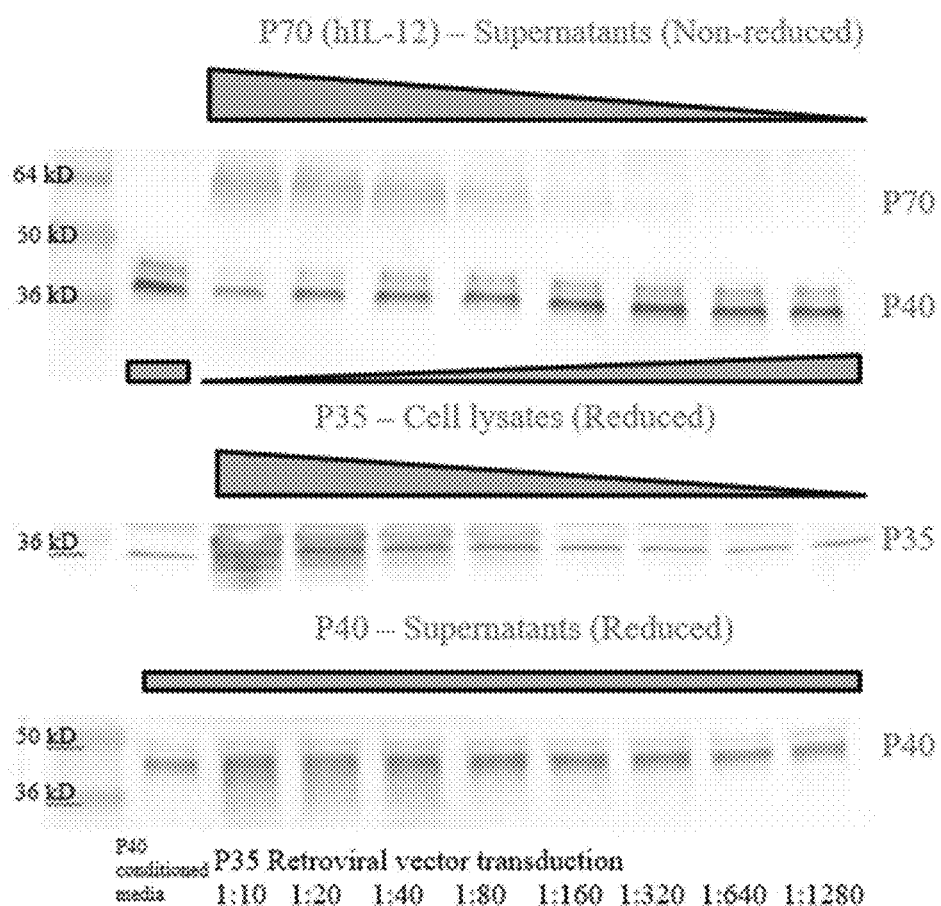
FIG. 19 illustrates Western blotting of IL-12 expression (human IL-12 or hIL-12). IL-12 (P70) expression was increased when expression of P35 increased. P70 expression was independent of P40 expression (e.g., P70 expression was increased with the increased expression of P35, while P40 expression was constant).
Figure 20:
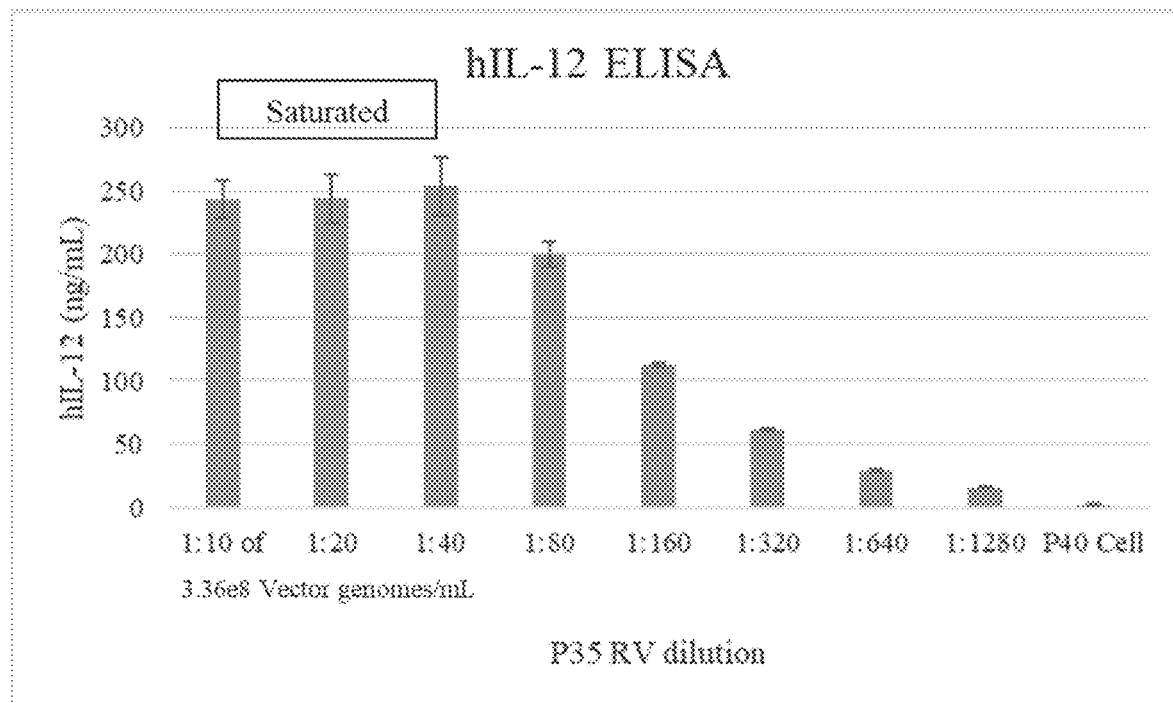
FIG. 20 illustrates an exemplary ELISA assay quantifying hIL-12 expression. Similar to FIG. 19, increased expression of P35 alone could increase expression of P70.

On day 1, A375 cells stably expressing P40 were seeded at 12,000 cells/cm² in a 96-well plate in 100 μL of growth media per 96-well. After cells were attached, the retroviral vector encoding P35 (3.36e8 vector genomes/mL) was transduced to A375-P40 stable cells with 8 μg/mL polybrene at serial dilutions (Table 3) in 100 μL of growth media. The day after transduction, fresh media was changed for the transduced A375 cells. Two days after media change, cell condition media were taken and subjected to WB and hIL-12 ELISA. Cells were grown for three more days, and cells and condition media were examined again by WB and hIL-12 ELISA. All ELISA samples were tested at 1:20 dilutions. FIG. 19 illustrates Western blotting of IL-12 expression (human IL-12 or hIL-12). IL-12 (P70) expression was increased when expression of P35 increased. P70 expression was independent of P40 expression (e.g., P70 expression was increased with the increased expression of P35, while P40 expression was constant). FIG. 20 illustrates an exemplary ELISA assay quantifying hIL-12 expression. Similar to FIG. 19, increased expression of P35 alone could increase expression of P70.

TABLE 3

Plate map showing a serial transduction of P35 retrovector to A375-P40 stable cells

| | 1 | 2 | 3 | 4 | 5 | 6 | 7 | 8 | 9 | 10 | 11 | 12 |
|---|---|---|---|---|---|---|---|---|---|---|---|---|
| A | A375-940 Cells | | | | | | | | | | | |
| B | | | | 1:10 | 1:20 | 1:40 | 1:80 | 1:160 | 1:320 | 1:640 | 1:1280 | |
| C | | | | 1:10 | 1:20 | 1:40 | 1:80 | 1:160 | 1:320 | 1:640 | 1:1280 | |
| D | | | | 1:10 | 1:20 | 1:40 | 1:80 | 1:160 | 1:320 | 1:640 | 1:1280 | |
| E | | | | 1:10 | 1:20 | 1:40 | 1:80 | 1:160 | 1:320 | 1:640 | 1:1280 | |

A375-P40 cells were seeded into a 96-well plate as described above. To avoid evaporation effects, rows A and H and columns 1 and 12 were not used but kept in growth media without cells throughout the experimental period. Columns 2 and 3 were seeded with A375-P40 cells without P35 retrovector transduction as a cell growth control. The condition media and cells from rows B-E were pooled for WB and ELISA testing. Rows F and G (not shown) were kept in growth media.

While the foregoing disclosure has been described in some detail for purposes of clarity and understanding, it will be clear to one skilled in the art from a reading of this disclosure that various changes in form and detail can be made without departing from the true scope of the disclosure. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method of treating cancer in a subject, comprising administering to the subject a first murine leukemia virus recombinant retroviral vector comprising a nucleic acid construct comprising a viral promoter operatively linked to a first polynucleotide sequence encoding a P40 subunit of Interleukin-12 (IL-12), a second polynucleotide sequence encoding a P35 subunit of IL-12, and a third polynucleotide sequence between the first and second polynucleotide sequences, wherein the third polynucleotide sequence encodes a cleavage site that facilitates cleavage between P40 subunit and P35 subunit, wherein route of the administering to the subject is selected from the group consisting of intravenous and intra-arterial routes, and wherein the recombinant retroviral vector induces a cell kill activity in the subject, thereby treating cancer in said subject.

2. The method of claim 1, wherein the cleavage site comprises a furin cleavage site.

3. The method of claim 2, wherein the furin cleavage site comprises an amino acid sequence of SEQ ID NO:3 or SEQ ID NO:12.

4. The method of claim 1, wherein the nucleic acid construct further comprises a fourth polynucleotide sequence between the first and second polynucleotide sequences, wherein the fourth polynucleotide sequence encodes a self-cleaving peptide.

5. The method of claim 4, wherein the self-cleaving peptide comprises an amino acid sequence selected from any one of SEQ ID Nos: 4-11 or a combination thereof.

6. The method of claim 1, further comprising:
a. administering to the subject a therapeutically effective amount of a pharmaceutical composition comprising a second recombinant retroviral vector comprising a nucleic acid construct comprising a polynucleotide sequence encoding a thymidine kinase; and
b. co-administering a nucleoside agent, wherein the nucleoside agent is at least one of ganciclovir, valganciclovir, acyclovir, valacyclovir, or penciclovir.

7. The method of claim 6, wherein the polynucleotide sequence encoding the thymidine kinase and the polynucleotide sequence encoding the P40 subunit of IL-12 and the P35 subunit of IL-12 are in the same recombinant retroviral vector.

8. The method of claim 6, wherein the polynucleotide sequence encoding a thymidine kinase and the polynucleotide sequence encoding the P40 subunit of IL-12 and the P35 subunit of IL-12 are in different recombinant retroviral vectors.

9. The method of claim 8, wherein the recombinant retroviral vector encoding the thymidine kinase and the recombinant retroviral vector encoding IL-12 are administered at different time points to the subject.

10. The method of claim 6, wherein the nucleoside agent is administered between 1 day and 2 days after administration of the second recombinant retroviral vector to said subject.

11. The method of claim 1, further comprising monitoring IL-12 level in the subject and inhibiting IL-12 expression in the subject when IL-12 level in the subject reaches a predetermined threshold.

12. The method of claim 1, wherein at least $1 \times 10^5$ total viral particles of the recombinant retroviral vector is administered cumulatively to said subject.

13. The method of claim 1, further comprising modulating an expression of IL-12 in said subject.

14. The method of claim 1, wherein administration of the first recombinant retroviral vector elicits reduced toxicity in the subject by at least 0.1 fold compared to toxicity induced by direct administration of IL-12 protein in said subject.

15. The method of claim 1, wherein administration of the first recombinant retroviral vector increases the efficacy of the treatment of the cancer in the subject by at least 0.1 fold compared to efficacy of the treatment of the cancer by direct administration of IL-12 protein in said subject.

16. The method of claim 1, further comprising delivering the retroviral vector to a cell or microenvironment associated with the cancer in said subject.

17. The method of claim 1, wherein the administration of the first recombinant retroviral vector decreases toxicity associated with administration of IL-12 protein in the subject without decreasing the efficacy of the treatment of the cancer by administration of the IL-12 protein in said subject.

* * * * *

```
                              SEQUENCE LISTING

Sequence total quantity: 16
SEQ ID NO: 1                   moltype = AA   length = 320
FEATURE                        Location/Qualifiers
source                         1..320
                               mol_type = protein
                               organism = Human alphaherpesvirus 1
SEQUENCE: 1
MASYPGHQHA SAFDQAARSR GHSNRRTALR PRRQQEATEV RPEQKMPTLL RVYIDGPHGM     60
GKTTTTQLLV ALGSRDDIVY VPEPMTYWRV LGASETIANI YTTQHRLDQG EISAGDAAVV   120
MTSAQITMGM PYAVTDAVLA PHIGGEAGSS HAPPPALTLI FDRHPIAALL CYPAARYLMG   180
SMTPQAVLAF VALIPPTLPG TNIVLGALPE DRHIDRLAKR QRPGERLDLA MLAAIRRVYG   240
LLANTVRYLQ CGGSWREDWG QLSGTAVPPQ GAEPQSNAGP RPHIGDTLFT LFRAPELLAP   300
NGDLYNVFAW ALDVLAKRLR                                                320

SEQ ID NO: 2                   moltype = AA   length = 12
FEATURE                        Location/Qualifiers
source                         1..12
                               mol_type = protein
                               organism = synthetic construct
SEQUENCE: 2
LQKKLEELEL DG                                                         12

SEQ ID NO: 3                   moltype = AA   length = 4
FEATURE                        Location/Qualifiers
source                         1..4
                               mol_type = protein
                               organism = synthetic construct
SEQUENCE: 3
RRKR                                                                   4

SEQ ID NO: 4                   moltype = AA   length = 18
FEATURE                        Location/Qualifiers
source                         1..18
                               mol_type = protein
                               organism = synthetic construct
SEQUENCE: 4
EGRGSLLTCG DVEENPGP                                                   18

SEQ ID NO: 5                   moltype = AA   length = 21
FEATURE                        Location/Qualifiers
source                         1..21
                               mol_type = protein
                               organism = synthetic construct
SEQUENCE: 5
GSGEGRGSLL TCGDVEENPG P                                               21

SEQ ID NO: 6                   moltype = AA   length = 19
FEATURE                        Location/Qualifiers
source                         1..19
                               mol_type = protein
                               organism = synthetic construct
SEQUENCE: 6
ATNFSLLKQA GDVEENPGP                                                  19

SEQ ID NO: 7                   moltype = AA   length = 22
FEATURE                        Location/Qualifiers
source                         1..22
                               mol_type = protein
                               organism = synthetic construct
SEQUENCE: 7
GSGATNFSLL KQAGDVEENP GP                                              22

SEQ ID NO: 8                   moltype = AA   length = 20
FEATURE                        Location/Qualifiers
source                         1..20
                               mol_type = protein
                               organism = synthetic construct
SEQUENCE: 8
QCTNYALLKL AGDVESNPGP                                                 20

SEQ ID NO: 9                   moltype = AA   length = 23
FEATURE                        Location/Qualifiers
source                         1..23
                               mol_type = protein
                               organism = synthetic construct
SEQUENCE: 9
GSGQCTNYAL LKLAGDVESN PGP                                             23
```

```
SEQ ID NO: 10              moltype = AA   length = 22
FEATURE                    Location/Qualifiers
source                     1..22
                           mol_type = protein
                           organism = synthetic construct
SEQUENCE: 10
VKQTLNFDLL KLAGDVESNP GP                                              22

SEQ ID NO: 11              moltype = AA   length = 25
FEATURE                    Location/Qualifiers
source                     1..25
                           mol_type = protein
                           organism = synthetic construct
SEQUENCE: 11
GSGVKQTLNF DLLKLAGDVE SNPGP                                           25

SEQ ID NO: 12              moltype = AA   length = 4
FEATURE                    Location/Qualifiers
source                     1..4
                           mol_type = protein
                           organism = synthetic construct
SEQUENCE: 12
RKRR                                                                   4

SEQ ID NO: 13              moltype = AA   length = 335
FEATURE                    Location/Qualifiers
source                     1..335
                           mol_type = protein
                           organism = Mus musculus
SEQUENCE: 13
MCPQKLTISW FAIVLLVSPL MAMWELEKDV YVVEVDWTPD APGETVNLTC DTPEEDDITW     60
TSDQRHGVIG SGKTLTITVK EFLDAGQYTC HKGGETLSHS HLLLHKKENG IWSTEILKNF    120
KNKTFLKCEA PNYSGRFTCS WLVQRNMDLK FNIKSSSSSP DSRAVTCGMA SLSAEKVTLD    180
QRDYEKYSVS CQEDVTCPTA EETLPIELAL EARQQNKYEN YSTSFFIRDI IKPDPPKNLQ    240
MKPLKNSQVE VSWEYPDSWS TPHSYFSLKF FVRIQRKKEK MKETEEGCNQ KGAFLVEKTS    300
TEVQCKGGNV CVQAQDRYYN SSCSKWACVP CRVRS                               335

SEQ ID NO: 14              moltype = AA   length = 218
FEATURE                    Location/Qualifiers
source                     1..218
                           mol_type = protein
                           organism = Mus musculus
SEQUENCE: 14
MCQSRYLLFL ATLALLNHLS LARVIRVIPV SGPARCLSQS RNLLKTTDDM VKTAREKLKH     60
YSCTAEDIDH EDITRDQTST LKTCLPLELH KNESCLATRE TSSTTRGSCL PPQKTSLMMT    120
LCLGSIYEDL KMYQTEFQAI NAALQNHNHQ QIILDKGMLV AIDELMQSLN HNGETLRQKP    180
PVGEADPYRV KMKLCILLHA FSTRVVTINR VMGYLSSA                            218

SEQ ID NO: 15              moltype = AA   length = 328
FEATURE                    Location/Qualifiers
source                     1..328
                           mol_type = protein
                           organism = Homo sapiens
SEQUENCE: 15
MCHQQLVISW FSLVFLASPL VAIWELKKDV YVVELDWYPD APGEMVVLTC DTPEEDGITW     60
TLDQSSEVLG SGKTLTIQVK EFGDAGQYTC HKGGEVLSHS LLLLHKKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYYSSSWS EWASVPCS                                       328

SEQ ID NO: 16              moltype = AA   length = 219
FEATURE                    Location/Qualifiers
source                     1..219
                           mol_type = protein
                           organism = Homo sapiens
SEQUENCE: 16
MCPARSLLLV ATLVLLDHLS LARNLPVATP DPGMFPCLHH SQNLLRAVSN MLQKARQTLE     60
FYPCTSEEID HEDITKDKTS TVEACLPLEL TKNESCLNSR ETSFITNGSC LASRKTSFMM    120
ALCLSSIYED LKMYQVEFKT MNAKLLMDPK RQIFLDQNML AVIDELMQAL NFNSETVPQK    180
SSLEEPDFYK TKIKLCILLH AFRIRAVTID RVMSYLNAS                           219
```